(12) United States Patent
Marks et al.

(10) Patent No.: US 10,435,343 B2
(45) Date of Patent: Oct. 8, 2019

(54) EFFICIENT CATALYTIC GREENHOUSE GAS-FREE HYDROGEN AND ALDEHYDE FORMATION FROM ALCOHOLS

(71) Applicant: Northwestern University, Evanston, IL (US)

(72) Inventors: Tobin J. Marks, Evanston, IL (US); Massimiliano Delferro, Chicago, IL (US); Peter C. Stair, Northbrook, IL (US); Tracy L. Lohr, Evanston, IL (US); Aidan R. Mouat, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 15/487,017

(22) Filed: Apr. 13, 2017

(65) Prior Publication Data
US 2017/0297988 A1    Oct. 19, 2017

Related U.S. Application Data

(60) Provisional application No. 62/322,094, filed on Apr. 13, 2016.

(51) Int. Cl.
*C07C 45/00* (2006.01)
*C01B 3/02* (2006.01)
*B01J 23/28* (2006.01)

(52) U.S. Cl.
CPC ............. *C07C 45/002* (2013.01); *B01J 23/28* (2013.01); *C01B 3/02* (2013.01); *C01B 2203/1082* (2013.01); *C01B 2203/1223* (2013.01); *C01B 2203/1229* (2013.01)

(58) Field of Classification Search
CPC ....... C07C 45/002; C07C 47/04; C07C 47/06; B01J 23/28; C01B 2203/1082; C01B 2203/1223; C01B 2203/1229; C01B 3/02
See application file for complete search history.

(56) References Cited

U.S. PATENT DOCUMENTS

| | | |
|---|---|---|
| 4,607,113 A | 8/1986 | Shum et al. |
| 2002/0197205 A1 | 12/2002 | Mahajan |
| 2003/0099593 A1 | 5/2003 | Cortright et al. |
| 2003/0159354 A1 | 8/2003 | Edlund et al. |
| 2003/0170171 A1 | 9/2003 | Cortright et al. |
| 2006/0269469 A1 | 11/2006 | Yeh |

(Continued)

FOREIGN PATENT DOCUMENTS

| | | |
|---|---|---|
| WO | 2003016211 A1 | 2/2003 |
| WO | 2005033003 A1 | 4/2005 |

(Continued)

OTHER PUBLICATIONS

Mouat et al. "Volatile Hexavalent Oxo-amidinate Complexes: Molybdenum and Tungsten Precursors for Atomic Layer Deposition" Feb. 26, 2016, Chem. Mater. 28, 1907-1919 (Year: 2016).*

(Continued)

*Primary Examiner* — Amber R Orlando
*Assistant Examiner* — Syed T Iqbal
(74) *Attorney, Agent, or Firm* — Bell & Manning LLC

(57) ABSTRACT

Catalytic preparation of hydrogen and aldehyde(s) from alcohols, including bioalcohols, without production of carbon monoxide or carbon dioxide.

24 Claims, 29 Drawing Sheets

(56) References Cited

U.S. PATENT DOCUMENTS

| | | | |
|---|---|---|---|
| 2007/0243128 A1 | 10/2007 | Reichman et al. |
| 2007/0269367 A1 | 11/2007 | Wolf |
| 2008/0025903 A1 | 1/2008 | Cortright |
| 2011/0305628 A1 | 12/2011 | Huang et al. |
| 2013/0071317 A1 | 3/2013 | Lee |
| 2013/0197245 A1 | 8/2013 | Umbarkar et al. |
| 2014/0370594 A1 | 12/2014 | Dumesic et al. |

FOREIGN PATENT DOCUMENTS

| | | | |
|---|---|---|---|
| WO | 2007001164 A1 | 1/2007 |
| WO | 2009059920 A2 | 5/2009 |
| WO | 2009129622 A1 | 10/2009 |
| WO | 2010033789 A2 | 3/2010 |
| WO | 2010078871 A1 | 7/2010 |
| WO | 2010098664 A1 | 9/2010 |
| WO | 2011072877 A1 | 6/2011 |
| WO | 2011149559 A2 | 12/2011 |
| WO | 2011158988 A1 | 12/2011 |
| WO | 2014012023 A1 | 1/2014 |
| WO | 2014078226 A1 | 5/2014 |
| WO | 2015063763 A1 | 5/2015 |

OTHER PUBLICATIONS

Tsilomelekis et al. "On the configuration, molecular structure and vibrational properties of MoOx sites on alumina, zirconia, titania and silica" 2013, Catal. Sci. Technol., 2013, 3, 1869-1888 (Year: 2013).*

Vellacheri et al. "Pt—MoOx-carbon nanotube redox couple based electrocatalyst as a potential partner with polybenzimidazole membrane for high temperature Polymer Electrolyte Membrane Fuel Cell applications", Mar. 2010, vol. 55, 8, p. 2878-2887 (Year: 2010).*

Rondon et al. "Characterization of Mo/C Catalysts by XRD, XPS, and TOF-SIMS", 1995, J. Phys. Chem. 99, p. 16709-16713 (Year: 1995).*

Lede, E. J. et al., "XANES Mo L-Edges and XPS Study of Mo Loaded in HY Zeolite", The Journal of Physical Chemistry B 2002, 106 (32), 7824-7831.

Lou, Y. et al., "SBA-15-supported molybdenum oxides as efficient catalysts for selective oxidation of ethane to formaldehyde and acetaldehyde by oxygen", Journal of Catalysis 2007, 247 (2), 245 255.

Dreisch, K. et al., "Synthesis of MO2Cl2(N,N,N',N'-tetramethylethylenediamine) (M=Mo and W) and crystal structure of WO2Cl2(N,N,N',N'-tetramethylethylenediamine)—an unprecedented coordination geometry in the WO2Cl2 Core", Polyhedron 1992, 11 (17), 2143-2150.

Mouat et al., "Volatile hexavalent oxo-amidinate complexes: Molybdenum and tungsten precursors for atomic layer deposition", Chemistry of Materials, Feb. 26, 2016 (e-pub), vol. 28, No. 6, 1907-1919.

Biradar et al., "Selective oxidation of aromatic primary alcohols to aldehydes using molybdenum acetylide oxo-peroxo complex ascatalyst", Tetrahedron Letters, 2009, vol. 50, No. 24, 2885-2888.

Sundstrom et al., "Computational and experimental study of the mechanism of hydrogen generation from water by a molecular molybdenum-oxo electrocatalyst," Journal of the American Chemical Society, 2012, vol. 134, No. 11, 5233-5242.

Lohr et al., "Efficient catalytic greenhouse gas-free hydrogen and aldehyde formation from aqueous alcohol solutions," Energy & Environmental Science, Mar. 28, 2017 (e-pub), vol. 10, No. 7, 1558-1562.

Mouat et al., "Reactivity of a carbon-supported single-site molybdenum dioxo catalyst for biodiesel synthesis," ACS Catalysis, Aug. 23, 2016 (e-pub), vol. 6, No. 10, 6762-6769.

* cited by examiner

EFFICIENT CATALYTIC GREENHOUSE GAS-FREE HYDROGEN AND ALDEHYDE FORMATION FROM ALCOHOLS

This application claims priority to and the benefit of application Ser. No. 62/322,094 filed Apr. 13, 2016—the entirety of which is incorporated herein by reference.

This invention was made with government support under DE-FG02-03ER15457 awarded by the Department of Energy. The government has certain rights in the invention.

BACKGROUND OF THE INVENTION

Primarily, hydrogen is produced industrially by catalytic steam reforming of nonrenewable methane at temperatures of 400-1000° C. and at steam partial pressures near 30 bar. Hydrogen production from renewable biomass is particularly challenging due to sluggish catalytic rates in water (the most common biomass contaminant) and catalyst deactivation. Furthermore, $H_2$ transportation and storage present safety issues. However, such concerns could be addressed using a carrier which released $H_2$ on demand, such as biomass-derived methanol, ethanol, or formic acid, all of which are compatible with direct alcohol fuel cell technologies. The state-of-the-art for sustainable, environmentally benign methanol and ethanol production typically employs biomass (e.g., cellulose) fermentation to "bioalcohols" containing ~10% alcohol in aqueous solution. Note that this bioalcohol is produced with negligible net carbon emission.

Regarding $H_2$ production from alcohols, the prior art literature describes several catalytic systems. A heterogeneous $Pt/Al_2O_3$ methanol reforming catalyst was reported to operate at 200-225° C. and pressures of 25-50 bar in aqueous media. In another study, using a homogeneous Ru pincer catalyst, 3 equiv. of $H_2$ can be produced from $MeOH+H_2O$ under moderate temperatures (72-95° C.), inert atmosphere, and ambient pressure. Note, however, that this conversion required strong base and is driven thermodynamically by stoichiometric $CO_2$/carbonate formation. The Ru pincer also operates in 9:1 $H_2O$:MeOH solution, albeit with a 18× reduction in TOF (265 h$^{-1}$) versus that in neat MeOH, (4719 h$^{-1}$). Other examples of homogeneous alcohol dehydrogenation by homogeneous Ru, Ir, and Fe catalysts bearing non-innocent ligands were reported. Many of these systems require stoichiometric strong base such as KOH for turnover and yield carbonates or $CO_2$ as co-products. While these homogeneous catalytic studies demonstrate that methanol and ethanol reforming are possible at low temperatures and pressures, they often require expensive metals and ligands requiring complex air-free synthesis and handling.

Roughly 30% of all methanol production worldwide is used to produce formaldehyde (~30 million tonnes annually), the starting material for a myriad of plastics and resins. Most formaldehyde is produced oxidatively using methanol, steam, and air at temperatures as high as 800° C. and at pressures near atmospheric. An efficient catalytic system that produced aldehydes and clean $H_2$ fuel from bioalcohols at moderate temperatures and pressures, without greenhouse gas co-products, would clearly be of great interest and represent an advancement in the art.

SUMMARY OF THE INVENTION

In light of the foregoing, it is an object of the present invention to provide methods for hydrogen and aldehyde production and/or catalytic compositions for use therewith, thereby overcoming various deficiencies and shortcomings of the prior art, including those outlined above. It would be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide a method for production of hydrogen from alcohols, including biomass-derived alcohols, for direct use, on demand without storage, transport and accompanying safety concerns.

It can be another object of the present invention to provide a method for facile production of aldehydes from alcohols or bioalcohols at moderate temperatures and pressures.

It can also be an object of the present invention, along or in conjunction with one or more of the preceding objectives, to provide a catalytic composition and/or system for concomitant production of hydrogen and aldehydes from alcohols, including bioalcohols, without production of carbon monoxide or carbon dioxide.

Other objects, features, benefits and advantages of the present invention will be apparent from this summary and the following descriptions of certain embodiments, and will be readily apparent to those skilled in the art having knowledge of hydrogen and aldehyde production from biomass sources and catalysts used therewith. Such objects, features, benefits and advantages will be apparent from the above as taken into conjunction with the accompanying examples, data, figures and all reasonable inferences to be drawn therefrom.

In part, the present invention can be directed to a composition comprising a molybdenum (Mo) dioxo moiety coupled to or on a support component comprising an oxygen moiety, such a component as can be selected from metal oxides (e.g., without limitation $Al_2O_3$ and $TiO_2$) and carbon based materials (e.g., without limitation, multi-walled carbon nanotubes and activated carbon). Such a composition can be characterized by the absence of chloride and/or $MoO_3$ moieties. In certain embodiments, such an Mo moiety can comprise up to about 5.0 wt % or more of such a composition. Alternatively, such a composition can be characterized as having an Mo density of about 0.22 Mo/nm$^2$ on such a support component. In certain such embodiments, such an Mo moiety can comprise up to about 2.1 wt % or more of such a composition. Alternatively, such a composition can be characterized as having an Mo density of about 0.10 Mo/nm$^2$ on such a carbon support component. Regardless, in certain embodiments, such a support component can comprise activated carbon.

In part, the present invention can also be directed to a method of producing hydrogen and an aldehyde from corresponding lower molecular weight alcohols. Such a method can comprise providing a reaction medium comprising an alcoholic hydrogen source, such as can be selected from but not limited to methanol, ethanol, isopropanol and combinations thereof; and contacting such a medium with an Mo dioxo composition of the sort described above or discussed elsewhere herein, such contact as can be for a time and/or at a temperature sufficient to oxidize such an alcohol to a corresponding aldehyde and produce hydrogen gas.

In certain embodiments, such an alcohol can be provided neat, in an organic solvent such as but not limited to toluene or as an aqueous solution thereof. In certain such embodiments, such an alcohol can be provided as an aqueous solution comprising up to about 90% water. Regardless, such a reaction medium can be at or brought to a temperature less than about 100° C. Without limitation, such a method can further comprise regeneration of such a catalyst composition by providing such an alcohol as an aqueous solution and/or washing such a catalyst composition with water after reaction with such an alcohol.

As a separate consideration, such a method can be incorporated into batch, semi-batch or continuous processes, the latter including but not limited to fluid bed reactors. Regardless, such a method can produce hydrogen, and a corresponding aldehyde, substantially without production of carbon monoxide and/or carbon dioxide.

In part, the present invention can also be directed to a transesterification method. Such a method can comprise providing a reaction medium comprising an ester component and an alcohol; and contacting such a medium with an Mo dioxo composition of the sort described above or discussed elsewhere herein, such contact as can be for a time and/or at a temperature sufficient for acyl C—O bond cleavage, to produce a corresponding alcohol from the alkoxy moiety of such an ester and transesterify the acid moiety of such an ester with an alcohol. In certain embodiments, such a reaction medium can be at or brought to a temperature less than about 100° C. Without limitation, such a method can further comprise regeneration of such a catalyst composition by providing an alcohol as an aqueous solution and/or washing such a catalyst composition with water after reaction therewith.

DETAILED DESCRIPTION OF CERTAIN EMBODIMENTS

As relates to certain non-limiting embodiments, this invention provides a heterogeneous catalytic system for base- and additive-free methanol and ethanol reforming that operates at high turnover frequencies under mild conditions (40-90° C. and 1 atm) with an inexpensive supported Mo catalyst that is air- and moisture-stable. Additionally, this system is active for aqueous alcohols, exhibits no deactivation over days under these conditions, and is selective towards valuable aldehydes with negligible production of greenhouse gases or fuel cell poisons ($CO_2$ or CO), conforming to requirements for formaldehyde production and direct alcohol fuel cell applications.

Figure 1A:
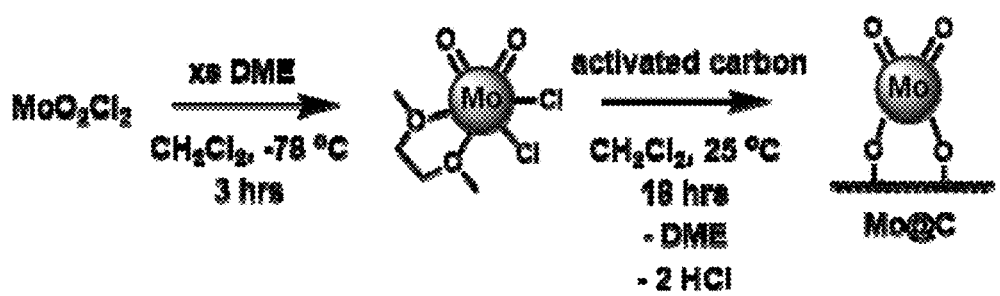
FIGS. 1A-D. (A) Mo@C catalyst synthesis. (B) Catalytic activity with MeOH and EtOH. (C) Evolved gas assays for: (C), neat MeOH+Mo@C. *=90° C. heating initiated; (D), 90% $D_2O$+10% EtOH+Mo@C, recycling runs. Ø=EtOH+$D_2O$ injection time.
Figure 1B:
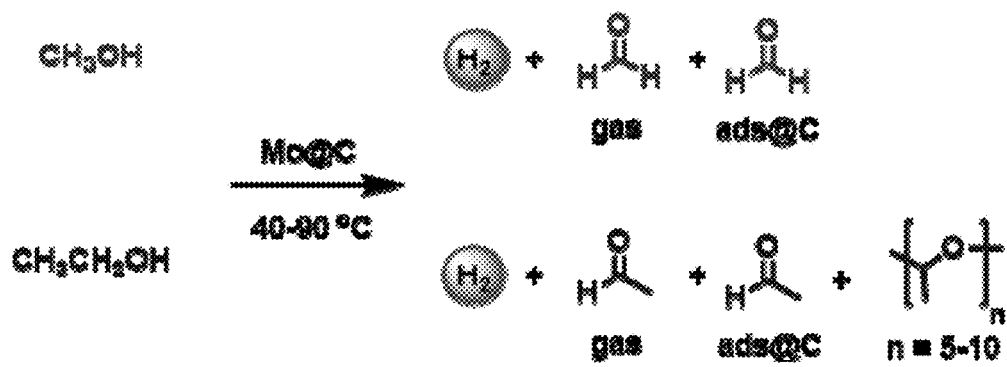
Figure 1C:
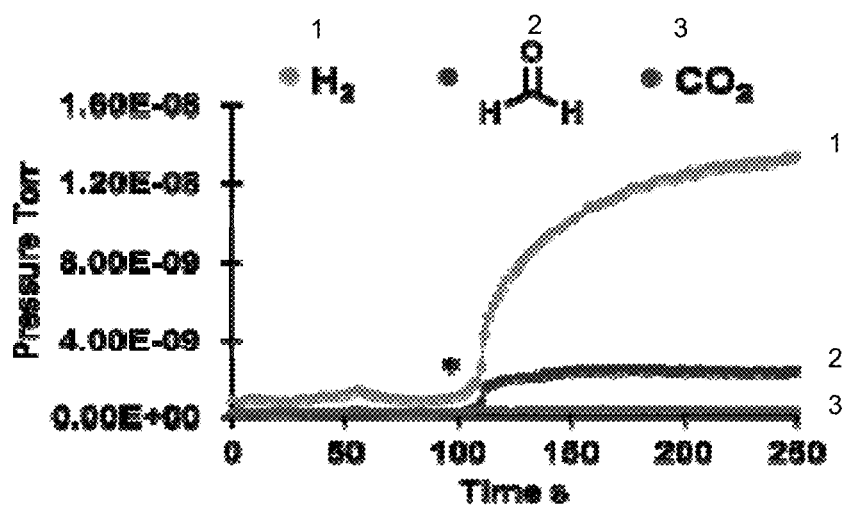
Figure 1D:
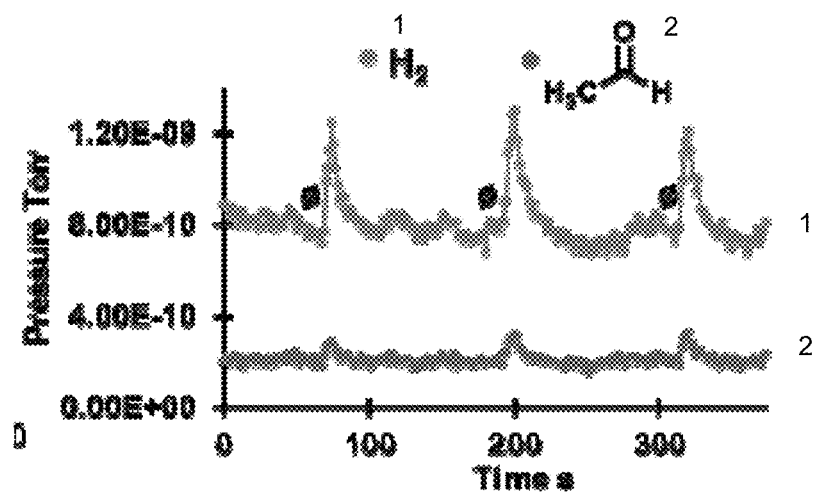
Figure 2A:
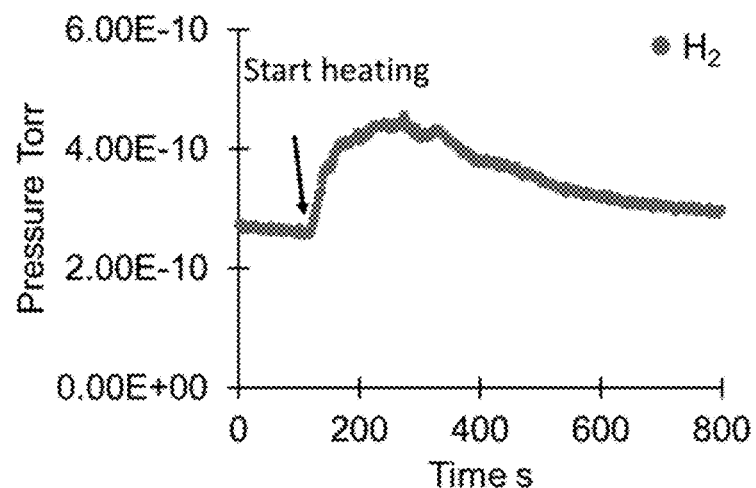
FIGS. 2A-B. Gas phase MS (Pressure vs Time) graphs of $H_2$ production from EtOH (1 mL) using Mo@C (0.030 g) at A. 60° C., and B. 40° C. Note: acetaldehyde not shown.
Figure 2B:
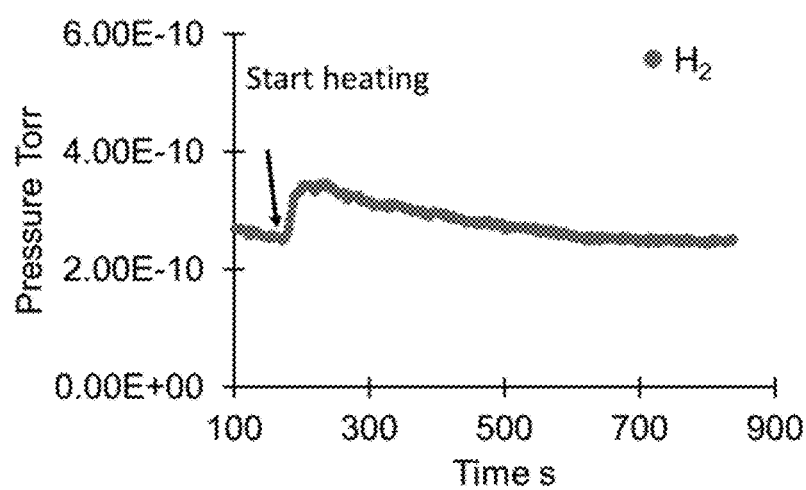
Figure 3A:
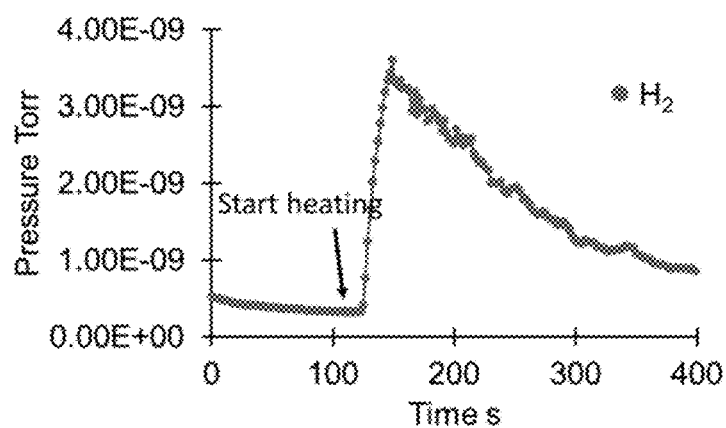
FIGS. 3A-B. Gas phase MS (Pressure vs Time) graphs of $H_2$ production from MeOH (1 mL) using Mo@C (0.030 g) at A. 60° C., and B. 40° C. Note: formaldehyde not shown.
Figure 3B:
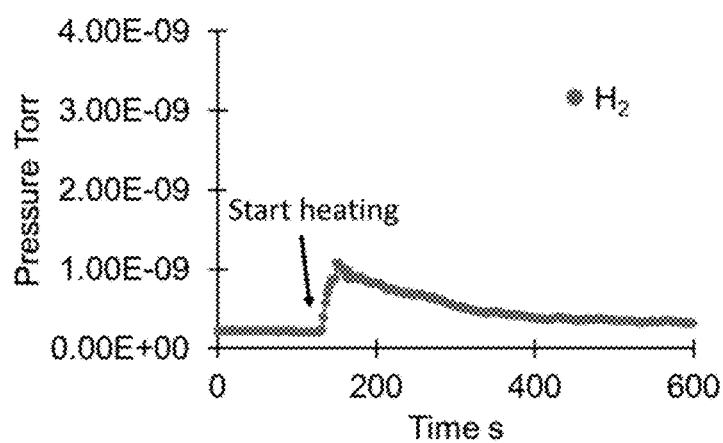

More specifically, this invention is, in part, directed to a molybdenum dioxo moiety coupled to or grafted on activated carbon, Mo@C, (as shown schematically in FIG. 1A), the nature of which was addressed by a variety of characterization techniques to determine the structure, surface area, and percentage of catalytically active sites in the material, and is discussed more fully, below. This catalyst is highly active for transesterification processes under high pressure at 60-90° C., rapidly mediates the dehydrogenation of neat, toluene-diluted, or aqueous MeOH and EtOH under inert atmosphere at 90° C. (FIGS. 1B-C) to yield 1.0 equiv. each of $H_2$ and the corresponding aldehyde (formaldehyde, b.p. −19° C.; acetaldehyde, b.p. 20° C.), as assayed by NMR, gas-phase mass spectrometry, and chemical titration with 2,4-dinitrophenyl hydrazine, while producing no detectable quantities of $CO_2$ or CO. Moreover, this catalytic system produces significant quantities of $H_2$ from both MeOH and EtOH at temperatures as low as 40° C. (FIGS. 2-3). Significant carbonate or formate production is not expected nor observed under these non-alkaline conditions.

Volumetric $H_2$ yields in this reaction are 90-100%/mol alcohol over 3 catalytic runs. Both XPS and $H_2$-Temperature Programmed Reduction (TPR), spectra not shown, indicate that the Mo@C unit remains intact after catalytic turnovers in ethanol. Furthermore, Mo@C can be recycled by filtering the hot EtOH suspensions, and maintains the dioxo structure. Note that activated carbon and commercial $MoO_3$ alone are catalytically inactive under these conditions (FIG. 4), consistent with the absence of $H_2$-TPR reduction events below 400° C. (As first appears in FIG. 4C, and used thereafter in several other figures, $MoO_2$/C is an alternate designation for a catalyst of this invention, a molybdenum dioxo moiety coupled or grafted to activated carbon, Mo@C.) For both alcohols, the origin of both the $H_2$ and aldehyde are confirmed by $CD_3OD/^{13}CH_3OH$ and $CD_3CD_2OD/^{13}CH_3CH_2OH$ labelling experiments (FIGS. 5-9).

Figure 10:
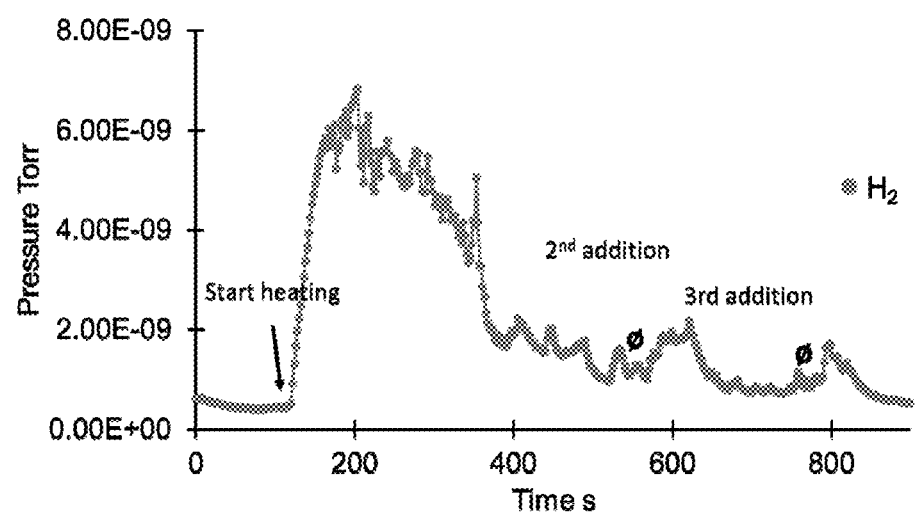
FIG. 10. Gas phase MS scan (pressure vs time) trace of successive MeOH additions (1.0 mL at 590 s and 790 s, each marked by ø) to Mo@C (0.030 g) at 90° C. in toluene showing that the catalyst deactivates over time in the absence of MeOH. Note: formaldehyde not shown.
Figure 11A:
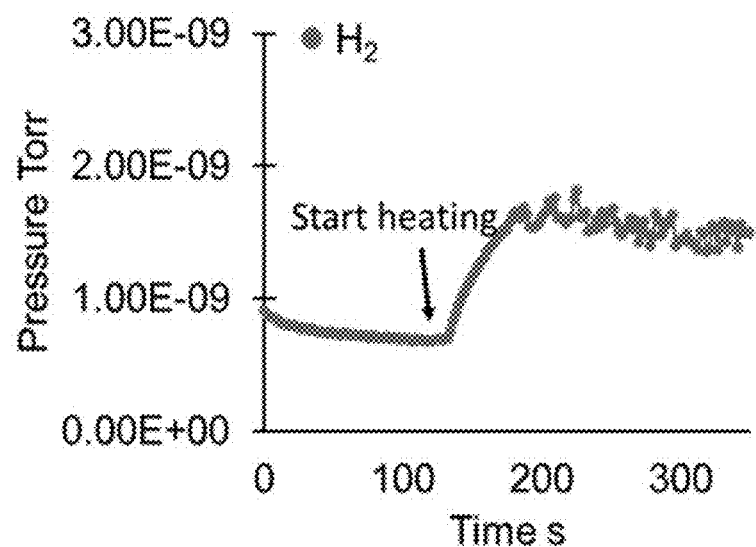
FIGS. 11A-B. (A) Gas phase MS (pressure vs time) traces monitoring MeOH (0.1 mL) and $H_2O$ (0.9 mL) addition to 0.030 g Mo@C (90° C. and 500 rpm). (B) Multiple additions of 1.0 mL MeOH (denoted by ø) to the same reaction mixture at 90° C. showing that the presence of $H_2O$ maintains catalytic activity. Note: formaldehyde not shown.
Figure 11B:
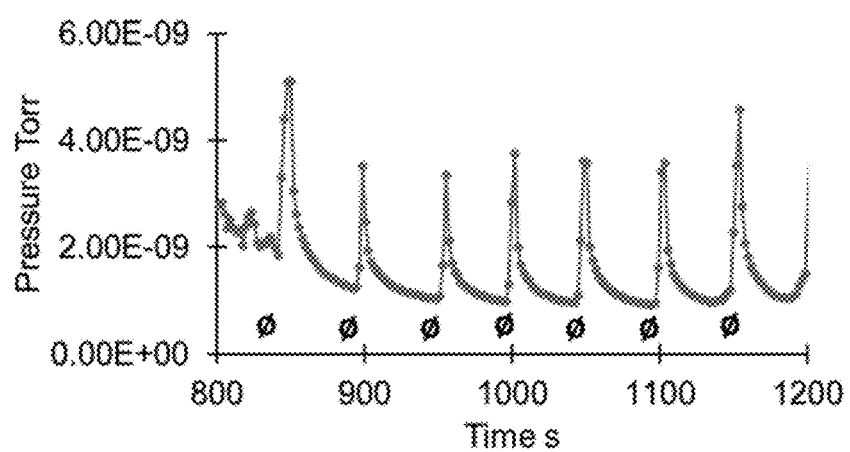
Figure 12A:
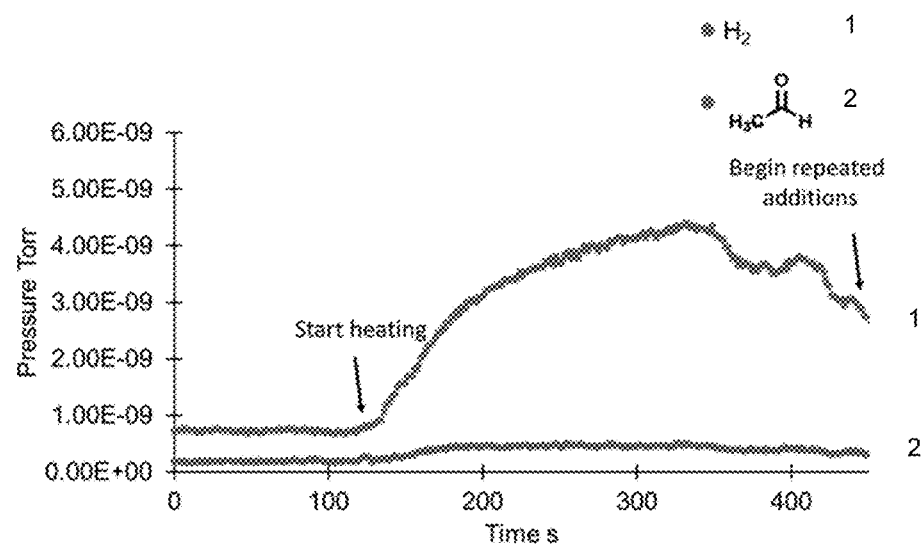
FIGS. 12A-B. Gas phase MS (pressure vs time) trace of successive EtOH additions (1.0 mL, denoted by ø in graph to Mo@C (0.030 g) added before all EtOH is consumed (90° C. and 500 rpm). A. Showing the point (time ~450 s) where another 1.0 mL of EtOH is added. B. Shows the successive 1.0 mL EtOH additions, 0).
Figure 12B:
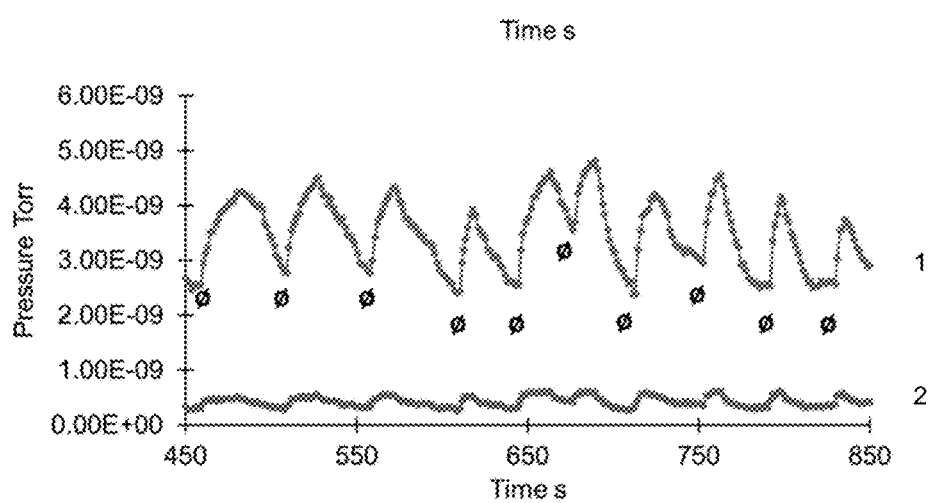
Figure 13:
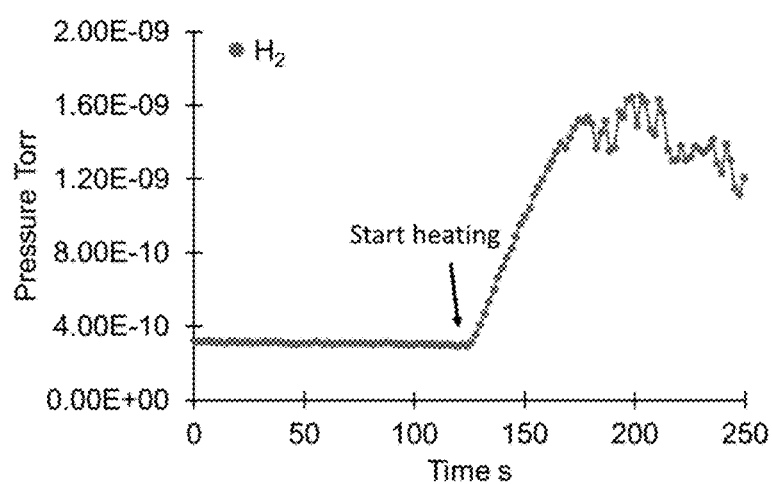
FIG. 13. Regenerated Mo@C catalyst, prepared by sonicating the inactive catalyst in water, with 1.0 mL EtOH at 90° C. Note: acetaldehyde not shown.

For alcohol+Mo@C reactions in toluene at 90° C., the catalyst undergoes slow deactivation upon complete alcohol consumption. Additional $H_2$ and gaseous aldehyde production is not observed when fresh alcohol is added (e.g., FIG. 10), suggesting that product formaldehyde and acetaldehyde formed in the reaction, possibly accelerated by protic activated carbon species, block/deactivate the Mo catalytic sites. In contrast, under repeated aqueous alcohol feed, the catalytic activity is stable, likely reflecting the solubility of the aldehyde products in water/alcohol (FIGS. 11 and 12). Solution phase $^1H$ NMR and Electrospray Ionization Mass Spectrometry (ESI-MS) of the preparative scale reaction products (not shown) confirm the presence of acetaldehyde oligomers, the majority having degrees of polymerization of 5-10. End-group analysis of these acetaldehyde oligomers shows the presence of —H and —OH termini, indicating that chain termination involves water. No formaldehyde oligomers are observed in the reaction solutions, indicating that formaldehyde is either on the surface of the catalyst or in the gas phase. Note also that the deactivated catalysts are readily regenerated by sonication in water for 5 min or evacuation at $10^{-2}$ Torr. These regenerated catalysts regain complete activity (FIG. 13), indicating that any deactivating adsorbed acetaldehyde monomer/oligomers and formaldehyde are effectively removed from the catalyst surface.

Catalytic experiments were next conducted in media mimicking "bio-alcohol," with $H_2O$:ROH ratios of 9:1 and 4:6. Here, aqueous EtOH and MeOH produce $H_2$ (Table 1 and FIG. 1C) with negligible catalyst deactivation, suggesting the aqueous medium solubilizes any aldehyde oligomers and suppresses the aforementioned blocking/deactivation. Thus, multiple alcohol additions to catalyst suspensions evidence no significant decline in catalytic turnover (FIGS. 1C and 11). Catalytic turnover frequencies (TOFs) were estimated from steady-state $H_2$ evolution data ($dPH_2/dt=0$) using calibrated gas-phase mass spectrometry and a semi-batch flow reactor (see, Examples 4 and 6) and are summarized in Table 1.

Due to the extremely high reaction rates and only slightly negative free energy of the overall reaction, it was expected that the calculated rates in Table 1 reflect transport limitations, probably at both the liquid-solid interface and involving by hydrogen gas transfer from the liquid phase to the gas phase. This is based on several experimental observations: 1) the hydrogen production is steady after the initiation of the reaction, as opposed to exhibiting any decay that would be expected from typical first-order kinetics. 2) In neat alcohol, the time required for and the hydrogen evolution to reach steady-state and the final partial pressure of hydrogen were both dependent on the quantity of alcohol concentration. In this case, larger amounts of soluble medium allow for larger amounts of hydrogen to leave the reactor, (resulting in higher hydrogen partial pressures) and require longer times to saturate, (resulting in longer delay times).

Figure 14:
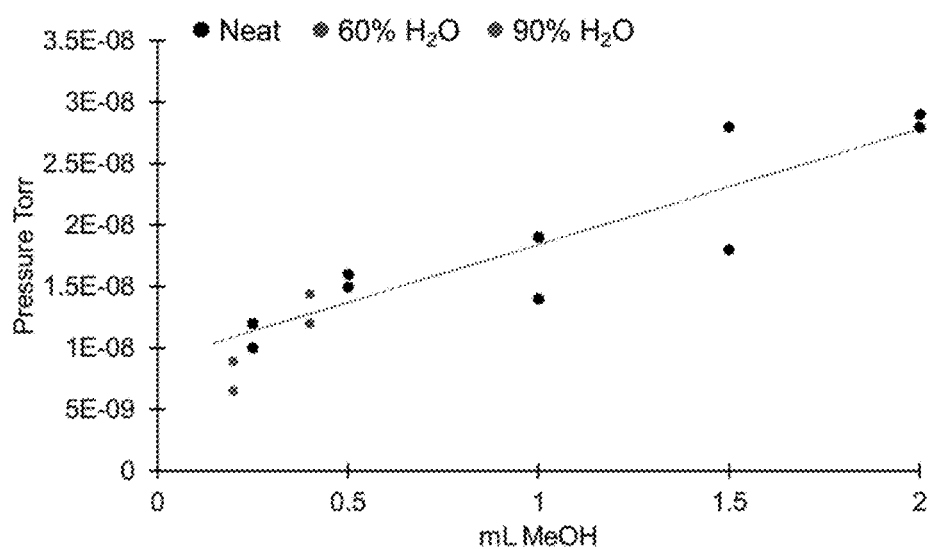
FIG. 14. $H_2$ pressure at steady state with varying MeOH
Figure 15:
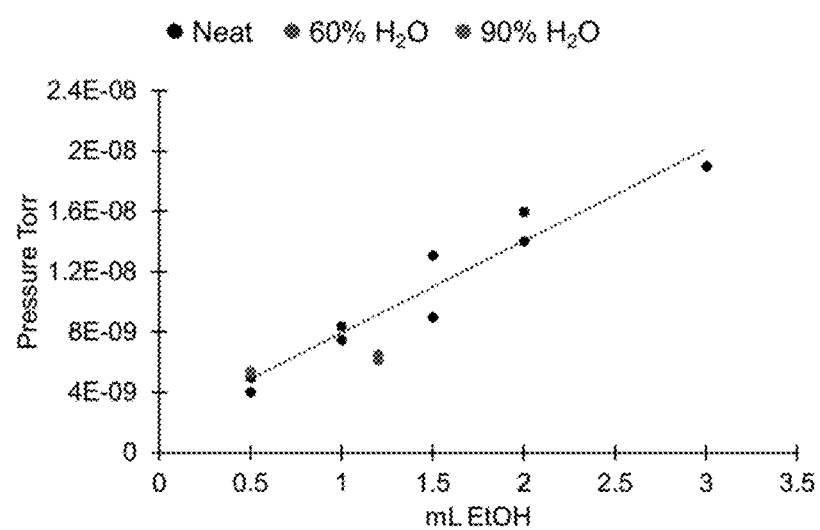
FIG. 15. $H_2$ pressure at steady state with varying EtOH.

The final $H_2$ partial pressure is unaffected by the amount of catalyst (see Table 2). The measured TOFs are affected only because of the catalyst weight normalization factor (see, Example 6 for calculation). This is demonstrated in entry 14 of Table 1 where using ~80× less catalyst results in a dramatic increase in TOF to 24,040 $h^{-1}$. Given this constraint, all data in Table 1 likely represent lower limits of the actual catalytic TOFs. Under aqueous conditions (60 and 90% $H_2O$), the steady-state rate of $H_2$ production is comparable to that for neat MeOH and EtOH (Table 1 entries 6-7 and 12-13, and FIGS. 14-15). Continuous heating of the catalyst system in MeOH:$H_2O$=20:80 at 90° C. over 5 days shows no decline in rate (see Table 3), validating the robustness of Mo@C under these operating conditions.

TABLE 1

Measured Mo@C catalysed $H_2$ production rates[a]

| Entry | ROH:$H_2O$ | mLROH | TOF ($h^{-1}$) |
|---|---|---|---|
| 1 | Neat MeOH | 2.0 | 668 ± 8 |
| 2 | Neat MeOH | 1.5 | 570 ± 88 |
| 3 | Neat MeOH | 1.0 | 454 ± 44 |
| 4 | Neat MeOH | 0.5 | 436 ± 8 |
| 5 | Neat MeOH | 0.25 | 356 ± 18 |
| 6 | MeOH 60:40 | 0.4 | 288 ± 20 |
| 7 | MeOH 10:90 | 0.2 | 189 ± 19 |
| 8 | Neat EtOH | 2.0 | 428 ± 18 |
| 9 | Neat EtOH | 1.5 | 358 ± 36 |
| 10 | Neat EtOH | 1.0 | 302 ± 8 |
| 11 | Neat EtOH | 0.5 | 280 ± 30 |
| 12 | EtOH 60:40 | 1.2 | 160 ± 4 |
| 13 | EtOH 10:90 | 0.5 | 148 ± 2 |
| 14[b] | Neat MeOH | 1.0 | 24,040 ± 214 |

TABLE 1-continued

Measured Mo@C catalysed $H_2$ production rates[a]

| Entry | ROH:$H_2O$ | mLROH | TOF (h$^{-1}$) |
|---|---|---|---|

[a]TOFs measured under steady state conditions and estimated per Mo center assuming 50% Mo active sites under semi-batch Ar(g) continuous flow (1 mL/s) at 90° C. with 30 mg of Mo@C (2.1 wt % Mo, 6.29 × 10$^{-6}$ mol). Reactions performed a minimum of 2x. Conversion determined by $H_2$ calibrated gas-phase MS.
[b]With 3.4 mg Mo@C (7.85 × 10$^{-8}$ mol Mo).

TABLE 2

TOF's while varying Mo@C (2.1 wt % Mo) at 90° C. (Madon-Boudart Test/Koros-Nowak Criterion).

| ROH | Catalyst (mg) | TOF (h$^{-1}$) |
|---|---|---|
| 1 mL MeOH | 75 | 140 ± 6 |
| 1 mL MeOH | 60 | 202 ± 8 |
| 1 mL MeOH | 45 | 268 ± 24 |
| 1 mL MeOH | 15 | 968 ± 56 |
| 1 mL MeOH | 7.5 | 11,378 ± 180 |
| 1 mL MeOH | 3.8 | 24,040 ± 214 |
| 2 mL EtOH | 60 | 78 ± 2 |
| 2 mL EtOH | 45 | 114 ± 4 |
| 2 mL EtOH | 15 | 338 ± 3 |
| 2 mL EtOH | 7.5 | 632 ± 28 |

TABLE 3

TOF's under continuous heating (2 mL $H_2O$) with 0.030 g of Mo@C at 90° C. (Total flow = 1 mL/s Ar gas).

| mL MeOH | TOF (h-1) | Day |
|---|---|---|
| 0.6 | 577 | 1 |
| 0.6 | 674 | 2 |
| 0.6 | 668 | 3 |
| 0.6 | 650 | 4 |
| 0.6 | 688 | 5 |

Catalytic $H_2$ generation from MeOH or EtOH, with formaldehyde or acetaldehyde co-generation, respectively, is estimated to be mildly endergonic (MeOH: $\Delta G_r$=+10.8 kcal mol$^{-1}$; EtOH: +6.8 kcal mol$^{-1}$ at T=90° C.). However, coupling to aldehyde condensation (e.g., to trimers) significantly lowers the unfavorability (EtOH: AG, =-33 kcal mol$^{-1}$; MeOH: AG, =+9.1 kcal mol$^{-1}$), and extrapolation to (CH$_2$O) lowers $\Delta G_r$ to +5.1 kcal mol$^{-1}$ for MeOH. Note, however, that while acetaldehyde oligomers are observed by reaction solution NMR and ESI-MS, significant quantities of the less stable formaldehyde oligomers are only observed in the gas phase (as formaldehyde) and not in the reaction mixture (see, Example 8 for characterization and discussion of generated formaldehyde). $H_2$ removal also provides a driving force to drive the reactions forward. This is evidenced by the lack of further $H_2$ production (past ~5%) when the system is closed.

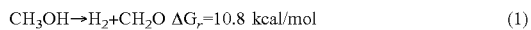

(1)

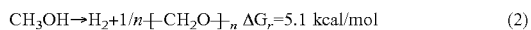

(2)

n=10

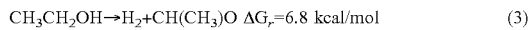

(3)

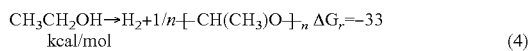

(4)

n=3

Based on the catalyst structural data, reaction stoichiometry/mass balance, isotopic labeling, and kinetic data, a plausible mechanistic scenario for $H_2$ production from EtOH is proposed in Scheme 1. It is not unreasonable to suggest that MeOH proceeds via a similar pathway. Ethanol activation involves substrate deprotonation by the Mo=O moiety with concomitant formation of a Mo-ethoxide (Scheme1, i, species b). Molybdenum oxo-hydroxo-alkoxides are known in the art and display catalytic activity or have been implicated in catalytic cycles. The activated ethoxide next undergoes β-hydride elimination to yield aldehyde and hydrido-hydroxide c, which subsequently eliminates $H_2$ to regenerate the MoO$_2$ active site a (Scheme 1, iii). The formation of a high-valent Mo—H species has literature precedent in addition of $H_2$, =B—H, and Si—H groups across the Mo=O bond of MoO$_2$Cl$_2$. This is also the species observed by XAS at 218° C. under an $H_2$ atmosphere. Similarly, $H_2$ generation from Mo=O species has been reported in the literature to proceed via Mo—H intermediates, further supporting the proposed cycle.

Scheme 1. Proposed Scenario for Mo@C mediated ethanol dehydrogenation

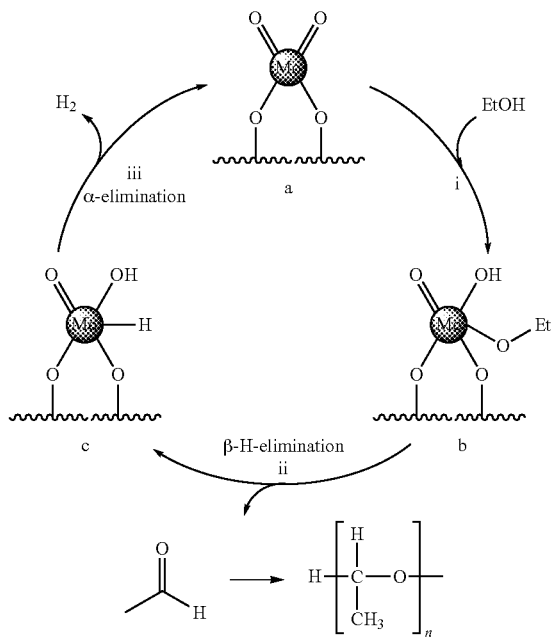

As discussed and demonstrated, this invention provides, in part, a highly active, supported, earth-abundant Mo-oxo catalyst for low-temperature $H_2$ and aldehyde formation from MeOH or EtOH. One equiv. $H_2$ is produced/mol alcohol, with concomitant formation of the corresponding aldehydes and negligible greenhouse gases. Under the current reaction conditions the TOFs reach up to 24,000 h$^{-1}$ for neat MeOH at 90° C. The intrinsic TOFs are doubtless greater than measurable using the present apparatus. This new catalytic system is base- and oxidant-free and not deactivated by water, hence is compatible with biomass-derived alcohol feedstocks. There is no detectable co-production of $CO_2$ or CO, making this system attractive for implementation in direct alcohol fuel cells and showing promise as a replacement catalyst for formaldehyde production that simultaneously generates a clean energy source. Further non-limiting embodiments can utilize this catalytic process under plug flow conditions.

Transesterification of Lower Alcohols and Esters.

As mentioned, above, an Mo dioxo catalyst of this invention can be used for transesterification. A variety of ester substrates were screened at 90° C. under 200 psi Ar(g) with 1 mol % Mo catalyst. Primary, secondary, and tertiary alkyl esters (1) undergo transesterification to produce the corresponding alcohols (2) and ethyl esters (3) under these conditions. Primary esters such as n-octyl acetate (Table 4 entry 1) and n-octyl octanoate (Table 4 entry 2) both react to form n-octanol, ethyl acetate, and ethyl octanoate, respectively. N-octyl acetate reacts roughly twice as fast (99% conversion at 16 hrs) as n-octyl octanoate (43% conversion at 16 hrs), most likely reflecting an increase in the difficulty of adsorption on the supported catalyst surface due to sterics. The secondary esters 2-octyl acetate and cyclohexyl acetate (Table 4, entries 3 and 4) react to similar conversions as primary n-octyl acetate, most likely due to similar steric effects of the substrates ability to adsorb on the surface of the catalyst. Replacing the acyl group with an aryl moiety (Table 4 entry 5) yields slightly higher conversion over the same time period. Subjecting γ-valerolactone (Table 4 entry 6) to transfer hydrogenolysis conditions in EtOH results in 25% conversion to ethyl butyrate. The benzylic 1,1-phenyl ethyl acetate undergoes 44% conversion after 16 hours producing the corresponding alcohol as well as the ketone in 8% yield (Table 4 entry 7). Presumably, the ketone forms from the dehydrogenation of the alcohol. The tertiary ester 1-methylcyclohexyl acetate also undergoes full conversion to the alcohol after 16 hours.

Using n-octyl acetate as a model substrate, the conversion followed over time yields a linear relationship, indicating that this reaction is zero order in substrate. The conversion of n-octyl acetate with varying amounts of Mo catalyst (1 to 3 mol % Mo) resulted in a linear relationship indicating the reaction is first order in Mo. The conversion of n-octyl acetate also exhibited a linear relationship with EtOH from monitoring the reaction with 1 through 4 molar equivalents of EtOH. Therefore, the overall rate equation is $k=[Mo]^1 [EtOH]^1$. Running the reaction in the presence of $H_2O$ (0 to 1 equivalents) did not result in reduction of catalytic activity at 90° C., indicating the supported MoC catalyst is not easily poisoned under these conditions. This catalytic acyl C—O bond cleavage reaction does not occur in the absence of catalyst or with the activated carbon support alone. Interestingly, crystalline $MoO_3$ catalyzes the conversion of n-octyl acetate to n-octanol at 90° C. in dry EtOH, but the TOF (h-1) is roughly ⅓ of that of the supported MoC catalyst under the same conditions. (These and additional results are summarized in Example 26 and Table 11, below.)

The conversion of n-octyl acetate was also monitored over different temperatures (60 to 90° C., Table 5) to generate and Eyring plot (FIG. 3) yielding activation parameters of $\Delta H^{\ddagger}=10.5$ (8) kcalmol$^{-1}$ and $\Delta S^{\ddagger}=-32$ (2) e.u. for this transformation (Table 6). The very low $\Delta H^{\ddagger}$ is in line with the low temperatures (60° C.) this reaction occurs at, and the activity of the supported Mo-oxo functionality. This is corroborated by the unprecedented low temperature (216° C.) of catalyst reduction. The large negative value of $\Delta S^{\ddagger}$ is likely a reflection of the energy required for the incoming substrate to coordinate and react at the supported Mo surface.

TABLE 4

Acetate Hydrogenation Substrate Scope

R—O—C(=O)—R' (1) → [Mo(Oxo)/C, 90° C., EtOH] → R—OH (2) + EtO—C(=O)—R' (3)

| | Substrates, 1 | Products, 2/3 | Time (h) | Conv. (Yield) % |
|---|---|---|---|---|
| 1 | n-C$_8$H$_{17}$OAc | n-C$_8$H$_{17}$OH | 1 | 17 (20) |
| | | | 16 | 99 (96) |
| 2 | n-C$_8$H$_{17}$OC(O)C$_7$H$_{15}$ | n-C$_8$H$_{17}$OH + EtO-C(O)-C$_7$H$_{15}$ | 16 | 43 (2, 43) (4, 40) |
| 3 | 2-octyl acetate (OAc) | 2-octanol (OH) | 16 | 47 (44) |
| 4 | cyclohexyl acetate (OAc) | cyclohexanol (OH) | 16 | 54 (49) |

TABLE 4-continued

Acetate Hydrogenation Substrate Scope

R–O–C(=O)–R' (1) →[Mo(Oxo)/C, 90° C., EtOH] R–OH (2) + EtO–C(=O)–R' (3)

| Substrates, 1 | Products, 2/3 | Time (h) | Conv. (Yield) % |
|---|---|---|---|
| 5: cyclohexyl benzoate | cyclohexanol + ethyl benzoate | 16 | 76 (2, 25) (4, 30) |
| 6: γ-valerolactone (5-methyl-dihydrofuran-2(3H)-one) | ethyl butyrate | 16 | 25 (25) |
| 7: 1-phenylethyl acetate | 1-phenylethanol + acetophenone | 16 | 44 (2, 14) (C=O, 8) |
| 8: 2-phenylethyl acetate | 2-phenylethanol | 16 | 99 (77) |
| 9: 1-methylcyclohexyl acetate | 1-methylcyclohexanol | 16 | 97 (97) |

[a]Conditions: 1 mmol substrate, 1 mol % Mo, 2 mL dry EtOH, 200 psi Ar(g), 500 rpm, conversion and yields determined by reference to mesitylene internal standard by $^1$H NMR spectroscopy, products were also confirmed by GC-MS analysis. Ethyl acetate was observed for reactions with an —OAc group by $^1$H NMR but was not quantified.

TABLE 5

Data for Eyring Plot.[a]

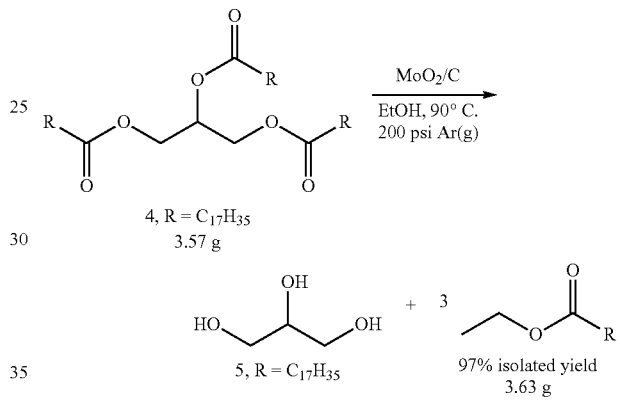

| Entry | Minutes | Conversion (%) | R-OH Yields | k (mmol/min) | Nt (h$^{-1}$) | Temp (K) |
|---|---|---|---|---|---|---|
| 1 | 60 | 17 | 20 | 0.283 | 1698 | 363.15 |
| 2 | 60 | 18 | 5 | 0.300 | 1800 | 363.15 |
| 3 | 60 | 19 | 4 | 0.317 | 1900 | 363.15 |
| 4 | 120 | 40 | 38 | 0.333 | 2000 | 363.15 |
| 5 | 120 | 36 | 37 | 0.300 | 1800 | 363.15 |
| 6 | 120 | 38 | 37 | 0.317 | 1900 | 363.15 |
| 7 | 120 | 26 | 24 | 0.217 | 1300 | 353.15 |
| 8 | 120 | 23 | 22 | 0.192 | 1150 | 353.15 |
| 9 | 120 | 26 | 25 | 0.217 | 1300 | 353.15 |
| 10 | 360 | 51 | 44 | 0.142 | 850 | 343.15 |
| 11 | 360 | 46 | 43 | 0.128 | 766.67 | 343.15 |
| 12 | 360 | 48 | 45 | 0.133 | 800 | 343.15 |
| 13 | 360 | 28 | 23 | 0.078 | 466.67 | 333.15 |
| 14 | 360 | 28 | 24 | 0.078 | 466.67 | 333.15 |
| 15 | 360 | 25 | 23 | 0.069 | 416.67 | 333.15 |

[a] 1 mmol n-octyl acetate, 1 mol % Mo, 2 mL anhydrous EtOH under 200 psi Ar(g) with stirring at 500 rpm.

TABLE 6

Activation parameters calculated from Eyring analysis for the conversion of n-octyl acetate to n-octanol at different temperatures. Brackets indicate ± calculated at the 95% confidence level.

| ln (k/T) | 1/T | ΔH$^{\ddagger}$ | ΔS$^{\ddagger}$ |
|---|---|---|---|
| −7.1571244 | 0.00275368 | 10.5 (8) kcalmorl$^{-1}$ | −32 (2) e.u |
| −7.0987888 | 0.00275368 | | |
| −7.0447216 | 0.00275368 | | |
| −6.9934283 | 0.00275368 | | |
| −7.0987888 | 0.00275368 | | |
| −7.0447216 | 0.00275368 | | |
| −7.3962881 | 0.00283166 | | |
| −7.5188904 | 0.00283166 | | |
| −7.3962881 | 0.00283166 | | |
| −7.7924461 | 0.00291418 | | |
| −7.8956303 | 0.00291418 | | |
| −7.8530707 | 0.00291418 | | |
| −8.3624924 | 0.00300165 | | |
| −8.3624924 | 0.00300165 | | |
| −8.475821 | 0.00300165 | | |

Activation parameters were calculated using the following Eyring expression (T=temperature, k=rate constant, R=gas constant, $k_B$=Boltzman constant, and h=Planck's constant).

$$ln\left(\frac{k}{T}\right) = -\frac{\Delta H^{\ddagger}}{R} \cdot \frac{1}{T} + \frac{\Delta S^{\ddagger}}{R} + ln\left(\frac{k_B}{h}\right)$$

Transesterification of Triglycerides.

On a preparative scale, tri-stearin, a long chain (4, R=n-$C_{17}H_{35}$) triglyceride, was subjected to transesterification conditions in EtOH at 90° C. with 1 mol % Mo metal loading (Scheme 2). After 6 hours, the reaction mixture was diluted with water and ethyl ester 5 was extracted with $CH_2Cl_2$. Ester 5 was recovered as a white solid in 97% isolated yield after removal of solvent in vacuo.

Scheme 2. Preparative scale triglyceride transesterification.

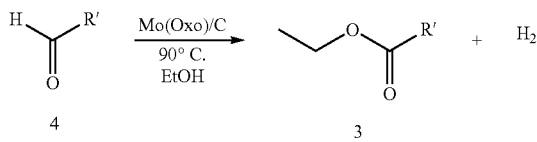

Oxidative Esterification of Lower Alcohols and Aldehydes.

Interestingly, aldehydes were also found to undergo oxidative esterification under the reaction conditions utilized. Both octanal and benzaldehyde were independently subjected to the reaction conditions for transesterification (Table 7, entries 1 and 2). Both aldehyde substrates were converted to the corresponding ethyl ester by the supported Mo catalyst. Aromatic cinnamaldehyde and para-tolualdehyde were also subjected to the reaction conditions, however, the enthalpy of desorption from the carbon surface was greater than that of acyl cleavage and either no yield was observed for these 2 substrates respectively (Table 7, entries 3 and 4).

TABLE 7

Oxidative esterification of aldehydes

| | Substrates, 4 | Products, 3 | Time (h) | Conv. (Yield) % |
|---|---|---|---|---|
| 1 | H-C(=O)-C$_7$H$_{15}$ | EtO-C(=O)-C$_7$H$_{15}$ | 2 | 65 (50) |

TABLE 7-continued

Oxidative esterification of aldehydes $$\text{H}\underset{\text{O}}{\overset{\text{R'}}{\diagup}} \quad \xrightarrow[\text{EtOH}]{\text{Mo(Oxo)/C} \atop 90°\text{ C.}} \quad \diagup\!\!\diagup\text{O}\underset{\text{O}}{\overset{\text{R'}}{\diagdown}} \quad + \quad \text{H}_2$$

4 → 3

| Substrates, 4 | Products, 3 | Time (h) | Conv. (Yield) % |
|---|---|---|---|
| 2  benzaldehyde | ethyl benzoate | 2 | 45 (25) |
| 3  p-tolualdehyde | — | 16 | 0 |
| 4  cinnamaldehyde | — | 16 | 0 |

[a]Conditions: 1 mmol substrate, 1 mol % Mo, 2 mL dry EtOH, 200 psi Ar(g), 500 rpm, conversion and yields determined by reference to mesitylene internal standard by $^1$H NMR spectroscopy, products were also confirmed by GC-MS analysis. Ethyl acetate was observed for reactions with an —OAc group by $^1$H NMR but was not quantified.

Recyclability of the Catalyst.

A recyclability test was performed in the transesterification of n-octyl acetate in neat ethanol a loading of 1 mol % Mo under our harshest conditions (90° C., 200 psi Ar, 500 rpm, 1-3 hours). After reaction, the catalyst was filtered out, dried, and added directly to a second reaction mixture. This procedure was repeated an additional time, for a total of three sequential reactions. The results are summarized in Table 8. Although a slight decrease in activity is observed ($N_t$=1930 to $N_t$=1800), the catalyst remains highly active even after its second recycling. After all three reactions, the 2.1 wt % Mo@C catalyst was analyzed for Mo content (by ICP-AES) and found to contain 1.7 wt % molybdenum, suggesting that some leaching occurs under our conditions; nevertheless, it does not impact the catalyst activity substantially.

TABLE 8

Catalyst recyclability tests. Conditions: 90° C., 200 psi Ar(g) and 500 rpm.

| Entry | Minutes | Conversion (%) | k (mmol/min) | Nt (h$^{-1}$) | Use # |
|---|---|---|---|---|---|
| 1[a] | 120 | 38.6 | 0.3217 | 1930 | 1 |
| 2[b] | 60 | 18 | 0.3 | 1800 | 2 |
| 3[c] | 180 | 55 | 0.306 | 1833.33 | 3 |

[a]0.4 mL n-ocryl acetate (2 mmol), Mo/C (0.0914 g, 1 mol % Mo), 4 mL EtOH.
[b]0.32 mL n-ocryl acetate (1.61 mmol), Mo/C (recovered from a: 0.0713 g, theoretical mmol of 0.0161 if still 2.1 wt %), 3.2 mL EtOH.
[c]0.3 mL n-octyl acetate (1.5 mmol), Mo/C (recovered from b: 0.0700 g, theoretical mmol of 0.0153 if still 2.1 wt % Mo), 3 mL EtOH.

A hot filtration experiment yielded confirmation of leaching but suggests the stability of the catalyst under air-free conditions. If the reaction mixture is filtered in open air while still hot (>60° C.), the solution turns blue and evinces further catalytic activity. To compensate for this, a sample of catalyst was refluxed in ethanol under nitrogen in a Schlenk flask. The supernatant liquid was then cannula-filtered into a second Schlenk flask under air-free conditions and allowed to cool. The cooled filtrate was then tested for catalytic activity in the reaction apparatus and found to be completely inactive. From this, it can be inferred that leached molybdenum only forms a catalytically active species upon heating in ambient conditions, and the supported Mo@C catalyst is the only active species under our conditions.

Catalyst Characteristics and Nature of the Active Site.

As discussed above and as can relate to several non-limiting embodiments of this invention, isolated dioxomolybdenum sites were grafted on a high surface area carbon support (Mo@C). XPS analysis and temperature-programmed reduction (TPR) with $H_2$ reveal the unique chemical character of the catalyst. It was shown that this catalyst is competent for liquid-phase alcohol transformations under mild conditions (60-90° C.), demonstrating high activity and selectivity. Specifically, Mo@C catalyzes the direct dehydrogenation of primary alcohols to liberate hydrogen; transesterification of primary and secondary esters with primary alcohols; and the oxidative esterification of aldehydes with alcohols. The catalyst operates efficiently in both organic and aqueous (up to 90% $H_2O$) solutions, suggesting it can be used for direct reactions with unrefined bioalcohols. Lastly, the catalyst exhibits no discernible deactivation and minimal leaching under reaction conditions, as determined by recyclability studies and XPS, PXRD, $N_2$ physisorption, and $H_2$ TPR. From these data, it was concluded the catalyst exhibits high potential for use in batch, semi-batch and continuous-flow applications for direction transformation of bioalcohols.

The carbon-supported dioxo-molybdenum catalyst was prepared via direct grafting of MoO$_2$Cl$_2$(dme) (dme=dimethoxyethane; prepared according to literature precedent and described, below. As would be understood in the art, other precursor starting materials can be used, such as MoO$_2$X$_2$, where X is bromide or iodide) onto an activated carbon support (Strem) in dichloromethane, yielding the proposed structure in FIG. 1A ("Mo@C"). Though there is no direct evidence for the lack of dimethoxyethane ligands on the resulting surface species, it seems unlikely that the ligand remains in light of its known lability. Absence of the —Cl ligand is confirmed via ICP and XPS. XPS reveals no species other than C, O, and Mo on the catalyst, although ICP-AES indicates the presence of sulfur, nitrogen, and phosphorous impurities in the support. The impurities in the carbon support were determined to be catalytically benign in control experiments. A typical catalyst contains about 2.1 wt % molybdenum. With the present preparation method, the maximum weight loading of molybdenum is about 5.0 wt %. The carbon support and Mo@C catalyst was fully characterized via PXRD, XPS, N$_2$ physisorption, and ICP-AES. After grafting of the Mo species, no difference in surface area, pore diameter, or crystallinity was detected in the catalyst. No MoO$_3$ phase was detected in the catalyst by PXRD, XPS, or H$_2$-TPR before or after catalytic reactions, suggesting the highly dispersed dioxo-molybdenum species remains stable under our conditions.

Due to the highly absorptive nature of the substrate, FTIR, Raman, and UV-vis spectroscopies were unable to provide evidence for the catalytically active site. However, the catalyst was well-characterized using XPS and TPR (FIG. 16) and PXRD (FIG. 17).

Figure 16A:
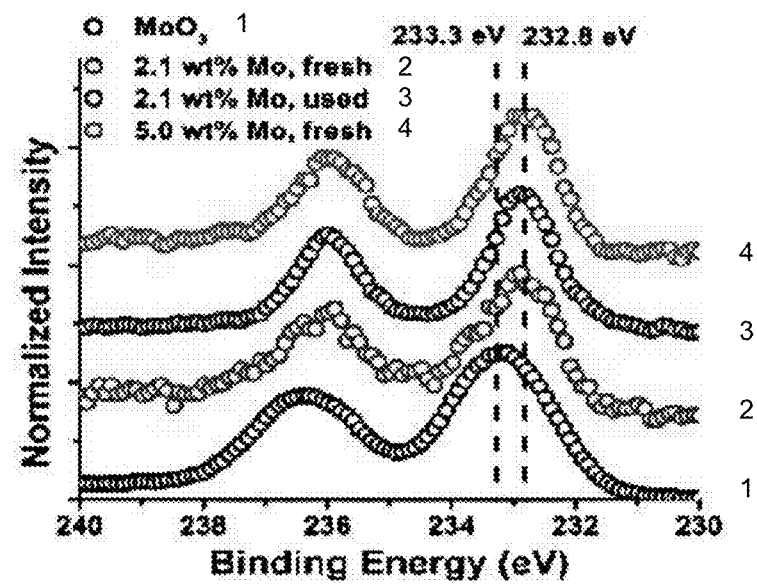
FIGS. 16A-C. (A) XPS spectrum of Mo(3d) peaks. $MoO_3$ used as a reference. (B) XPS spectrum of O(1s) peaks. (C) TPR traces of reference $MoO_3$ (1), carbon (2), fresh 2.1 wt % Mo (3), and used 2.1 wt % Mo (4).
Figure 16B:
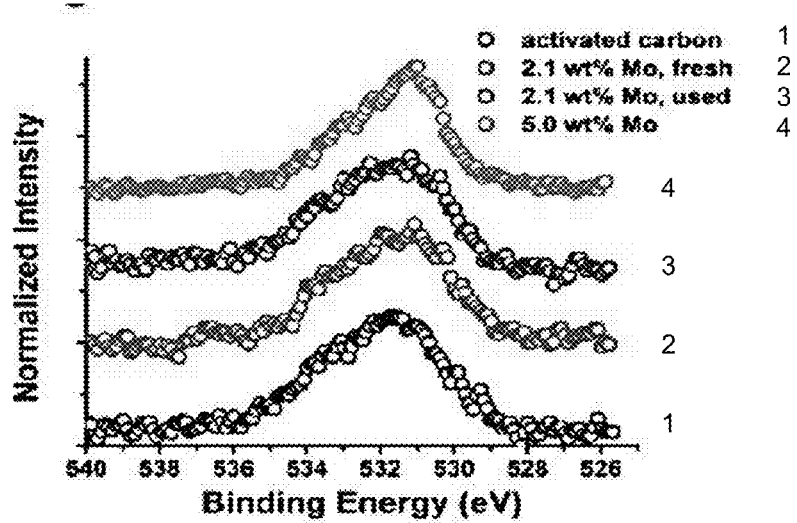
Figure 17:
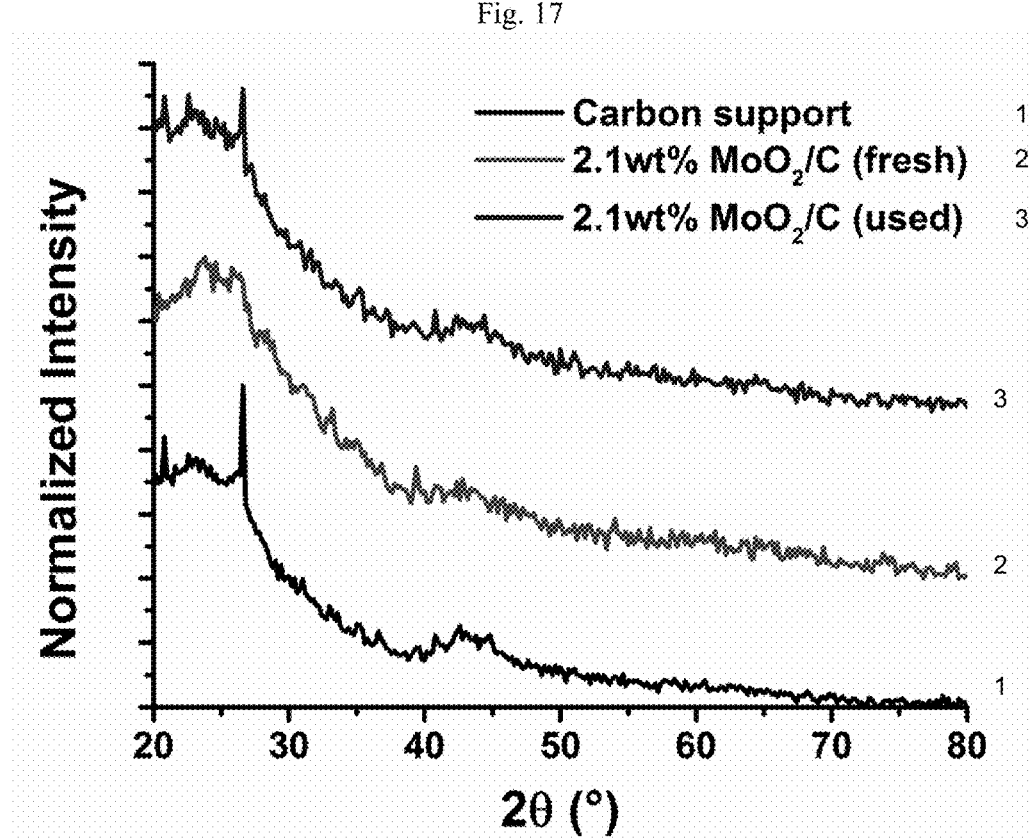
FIG. 17. Powder X-ray diffraction patterns of carbon materials. (1) Diffractogram of the activated carbon support. (2) Diffractogram of a 2.1 wt % $MoO_2C$ catalyst, freshly prepared. (3) Diffractogram of a 2.1 wt % Mo@C catalyst after use.
Figure 18A:
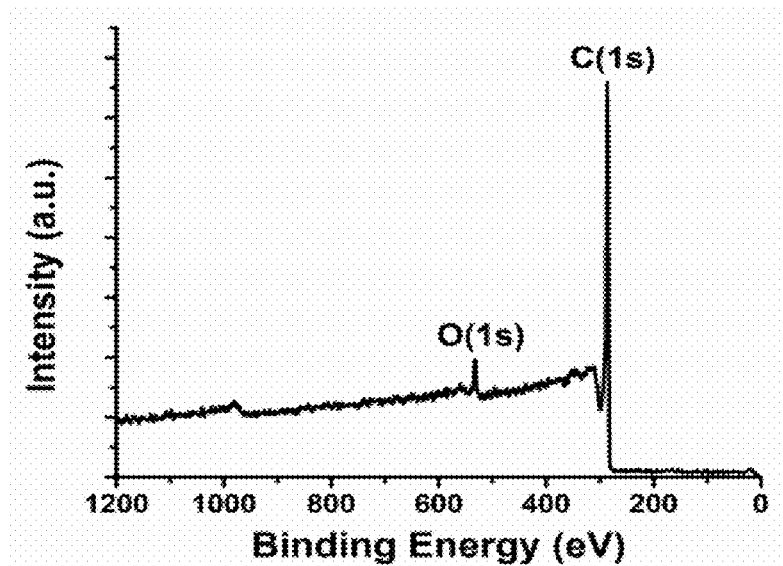
FIGS. 18A-C. XPS characterization of carbon support. (A) Survey spectrum of carbon support. No heteroatoms except for O detected. (B) C(1s) spectrum of the carbon support. (C) O(1s) spectrum of the carbon support.
Figure 18B:
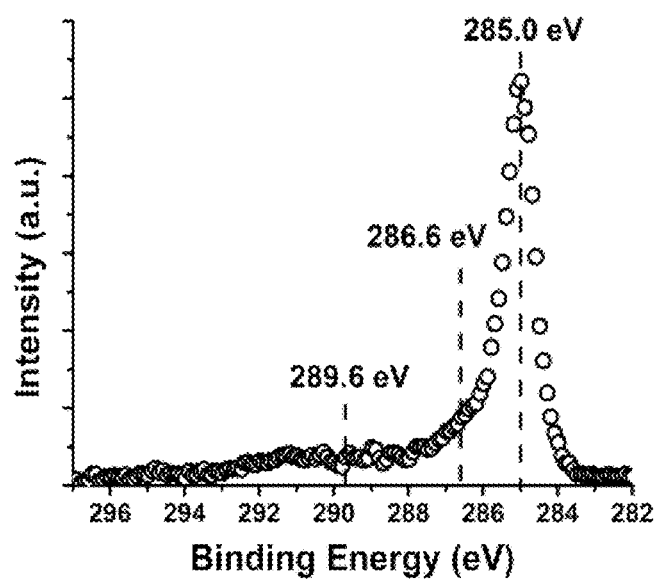
Figure 18C:
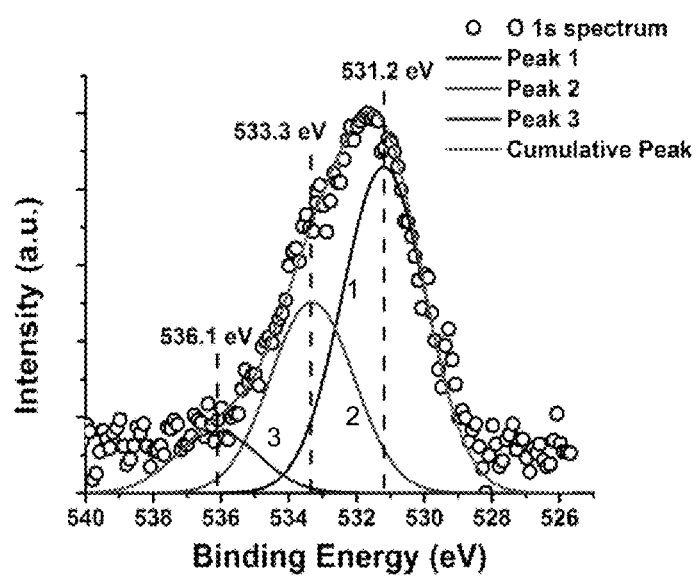
Figure 19:
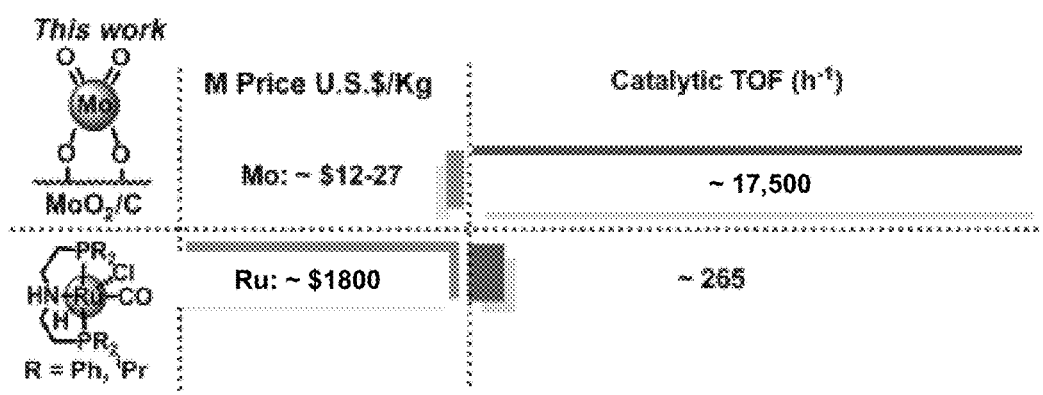
FIG. 19. Cost and $H_2$ production rate from a 1:9 MeOH:$H_2O$ mixture at 90-95° C. for comparing a prior art alcohol dehydrogenation catalyst with a catalyst composition of the present invention, in accordance with certain non-limiting embodiments of this invention. The prior art Ru system requires a KOH or NaOH co-catalyst; metal costs available from Metal Prices website on Mar. 21, 2016. (It should be understood that TOFs available through use of this invention can be well in excess of 17,500, as demonstrated elsewhere herein.)

As shown in FIG. 16A, the binding energy of Mo$^{VI}$ in MoO$_3$, measured as a reference in the same spectrophotometer, is found to be 233.3 eV. The binding energy of Mo$^{VI}$ in the present Mo/C catalyst is found to be 232.8 eV, shifted from the bulk MoO$_3$ environment but consistent with literature reports of hexavalent Mo species. No change in the binding energy of the catalyst is observed as a function of loading, nor after the catalyst is recovered from reaction. Importantly, no molybdenum carbide or oxycarbide phase was detected, suggesting the active site remains to be the highly dispersed dioxo-molybdenum species. The C(1s) peak (FIG. 18B) contains three contributions. The bulk graphitic carbon is referenced to 285.0 eV. Additional peaks appear at 286.6 eV and 289.6 eV. These species are assignable to carbon species in —C=O and —COOH environments, as has been previously observed in the literature. The O(1s) peak of the support (FIG. 16B, FIG. 18C) can be deconvoluted into three components at 531.2 eV, 533.3 eV, and 536.1 eV, as shown in FIG. 18C. These peaks can be assigned to carbonyl oxygen species, alcohol or etheric oxygen species, and adventitious water respectively, consistent with the species observed in the C(1s) spectrum.

Figure 16C:
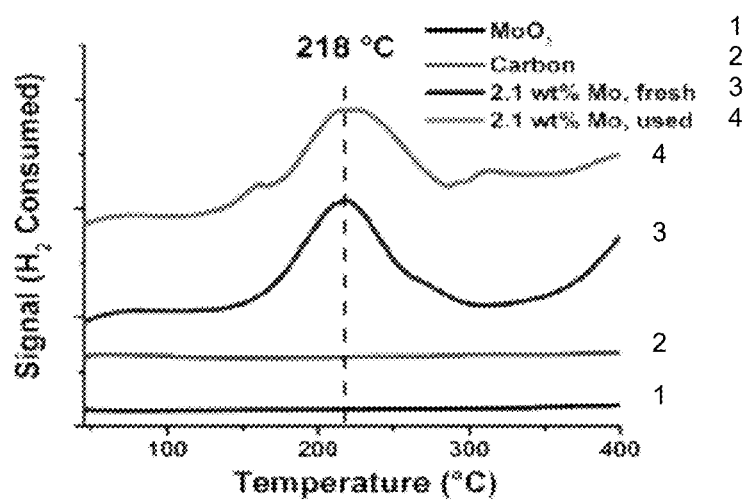

The temperature-programmed reduction (TPR) profile in H$_2$ of the catalyst is shown in FIG. 16C. Both the carbon support and reference MoO$_3$ shown no reduction events below 400° C., although MoO$_3$ was observed to reduce at higher temperatures (>550° C.). The carbon support begins to consume hydrogen independently above 450° C., thus the analysis was limited to the region below 400° C. The fresh 2.1 wt % Mo@C catalyst shows a single reduction event at 218° C., suggesting that grafted dioxo-molybdenum sites are highly reducible in comparison to the molybdenum sites found on MoO$_3$. The same catalyst was tested after reaction and little change is observed in its TPR profile. This evidence suggests that the active site remains intact throughout catalysis, in support of the high activity and recyclability found for Mo@C catalysts.

In contrast to traditional preparation methods like incipient wetness impregnation, which has yielded Mo/C catalysts of up to 30 wt % Mo in previous studies, the preparation of Mo@C catalysts by grafting reaches a maximum concentration of about 5 wt % Mo. The maximum surface density of Mo-sites is thus about 0.22 Mo/nm$^2$. Although most reactions herein reported were run with a catalyst having 0.10 Mo/nm$^2$, no substantial difference in reactivity was observed at either loading, suggesting the sites remain uniformly dispersed up to the maximum loading at 0.22 Mo/nm$^2$. It is noted that typical dispersions of MoO$_x$ species supported on refractory metal oxides are in the range of 0.15-5 Mo/nm$^2$, but maximum activity is typically obtained at loadings close to a monolayer, suggesting substantial chemical difference between traditional MoOx preparations of the prior art and Mo@C catalysts of the present invention.

As is common for activated carbon materials, BJH analysis of N$_2$ physisorption indicates both meso- and microporosity in the resultant catalyst. As the porosity does not change with Mo grafting, it can be inferred that the Mo sites do not locally block micropores in the carbon. In addition, XPS is capable of detecting Mo species in the catalyst (FIG. 16A). The sampling depth of XPS is no more than 10's of nanometers, but the mesoporous nature of the carbon suggests that the chemical surface area exists throughout the bulk of the material, thus making localization of molybdenum at the outer surface of the carbon unlikely. Thus, it is suggested that the dioxo-molybdenum species is well-dispersed throughout the bulk of the carbon support, an interpretation consistent with the lack of change in BET and BJH analysis of N$_2$ physisorption after the grafting reaction. In contrast, while ICP-AES indicates the presence of sulfur, nitrogen, and phosphorous impurities, XPS does not detect these heteroatoms, indicating that they are localized deep in the carbon support and are not similarly dispersed throughout. Therefore, it is believed that the molybdenum sites are grafted onto carbon through the C—O functionalities detected by XPS (FIG. 16B). The relatively low saturation point for surface Mo (0.22 Mo/nm$^2$) suggests that the grafting reaction is surface-controlled and appropriate reactive surface sites are in low profusion.

Previous studies indicate that at high dispersions, the dominant Mo surface structure is the tetrahedral dioxo species. In Mo@C catalysts, Mo(3d) XPS provides further evidence for the monomeric character of the present dioxo-molybdenum sites. It is known from the literature that molybdenum oxide clusters exhibit size-dependent binding energy shift effects.

Molybdenum species in small oligomeric or polymeric clusters shift the binding energy of the Mo$^{VI}$(3d) peak to binding energies higher than that observed for Mo$^{VI}$ in MoO$_3$. In contrast, for an Mo species constrained from polymerizing (e.g., when stabilized in Y zeolite) this shift is not observed. (Lede, E. J.; Requejo, F. G.; Pawelec, B.; Fierro, J. L. G., XANES Mo L-Edges and XPS Study of Mo Loaded in HY Zeolite. *The Journal of Physical Chemistry B* 2002, 106 (32), 7824-7831.) Comparison to reference MoO$_3$ in the spectrometer, as well as literature values, indicates that the catalyst Mo species is indeed hexavalent with no detectable Mo$^V$ or Mo$^{IV}$ species; therefore, the shift of the Mo(3d$_{5/2}$) peak to the lower binding energy of 232.8 eV is indicative of monomeric Mo species.

Temperature-programmed reduction (TPR-$H_2$) of the Mo species confirms XPS analysis (FIG. 16C). Mo@C shows a single low-temperature reduction event at 218° C., suggesting the Mo active site to be both highly uniform and highly reducible. It is believed that 218° C. is the lowest reported reduction temperature of a supported Mo species. For example, the Wang group reported reductions of $MoO_x$/SBA-15 at surface densities from 0.25-10.24 Mo/$nm^2$ and found no reduction events below 400° C. (See, e.g., Lou, Y.; Wang, H.; Zhang, Q.; Wang, Y., SBA-15-supported molybdenum oxides as efficient catalysts for selective oxidation of ethane to formaldehyde and acetaldehyde by oxygen. *Journal of Catalysis* 2007, 247 (2), 245-255.) In addition, reduction temperature was found to decrease with increasing oligomerization, suggesting monomeric species to be the least reducible under the reported conditions.

The stability of highly-dispersed dioxo-molybdenum sites is confirmed via recyclability studies and further supported by spectroscopy and $H_2$-TPR measurements on used catalysts. XPS indicates no binding energy shift in the Mo species after catalysis. Similarly, $H_2$-TPR indicates that the Mo species remains uniform and highly reducible. Lastly, the activity of the Mo@C catalyst does not diminish significantly even after repeated use.

Catalytic scope and mechanism. Primary esters such as n-octyl acetate (Table 11, entry 4) and n-octyl octanoate (Table 11, entry 5) react to form n-octanol, ethyl acetate, and ethyl octanoate respectively. (See, Example 26.) N-octyl octanoate reacts at roughly half the rate (43% conversion at 16 h) as n-octyl acetate (99% conversion at 16 h), due most likely to increased steric hindrance. In n-octyl octanoate the fall in rate is more pronounced than in the case of the very sterically challenged and electronically different 1-methylcyclohexyl acetate (Table 11, entry 12), which reacts at a rate comparable to n-octyl acetate (97% conversion in 16 h). The secondary esters 2-octyl acetate and cyclohexyl acetate (Table 11, entries 6 and 7) react more slowly than the primary n-octyl acetate, excluding substitution at the alkyl position as a factor in rate. The lack of a distinct trend in degree of substitution implies the mechanism does not proceed through a carbocation intermediate, excluding C—O cleavage or deacylation as a reaction pathway and suggesting instead the mechanism presented in Scheme 3. Note that replacing the acyl group with an aryl moiety increases the rate (Table 11, entry 8). In the case of entry 8, although overall conversion is high (76%), the yield of recovered product is reduced (25% for the alcohol, 30% for the ethyl ester). This is likely a result of adsorption to the catalyst surface, although whether it is of the substrate or an aldehyde reaction intermediate is unclear. Subjecting γ-valerolactone (Table 11 entry 9) to transesterification conditions in EtOH results in 25% conversion to ethyl butyrate. Benzylic 1-phenethyl acetate undergoes 44% conversion in 16 hours producing the corresponding alcohol as well as the ketone in 8% yield (Table 11, entry 10). Again, the final yield of the aromatic product is low. The ketone presumably forms from the dehydrogenation of the alcohol. In contrast to other aromatic substrates, entry 11 (Table 11) is recovered in good yield (77%), suggesting that adsorption of the substrate to the catalyst surface does not occur with all substrates and may require an α,β-unsaturated carbonyl functionality.

The transesterification of the long chain (n-$C_{17}H_{35}$) triglyceride tri-stearin with ethanol to produce the corresponding ethanoate and glycerol was performed on a large scale (Scheme 3). After aqueous workup followed by extraction with $CH_2Cl_2$, the ethanoate product (5) was isolated as a white solid in 97% yield, indicating that this catalyst and method is a viable alternative to harsh alkaline and/or Brønsted acidic process for the production of biodiesel.

A proposed catalytic cycle for the transesterification of esters with ethanol is shown in Scheme 3. The catalytic cycle follows those previously suggested in the literature and bears similarities to that of the well-studied mechanism for transesterification by oxo-tin compounds such as di-n-butyltin oxide (DBTO). Activation of ethanol occurs via $H^+$ abstraction by the Mo═O fragment (Scheme 3, species a) and concomitant formation of a Mo-ethoxide species (Scheme 3, species b). Molybdenum oxo-hydroxo-alkoxides are known in the literature and the resulting structures have exhibited catalytic activity and/or have been implicated in catalytic mechanisms. Since the present kinetic studies show the reaction to be first-order in EtOH concentration, it is reasonable to propose addition of one equiv. EtOH to the pre-catalytic molybdenum-dioxo site to form the active species (Scheme 3, b). When the activated Mo-ethoxide species coordinates an ester (as in Scheme 3, i), the activated ester carbonyl (Scheme 3, c) undergoes nucleophilic attack by the ethoxide to yield the ethyl ester product (Scheme 3, ii) and a new Mo—OR fragment (Scheme 3, d). Further exchange of the Mo—OR fragment with EtOH (Scheme 3, iii) regenerates the activated Mo-OEt fragment (Scheme 3, c) and enables catalytic turnover. Since both stability and recyclability of the catalyst has been established, it is proposed that the $MoO_2$ fragment (Scheme 3, a) can be recovered via elimination of an equivalent of EtOH to retain its chemical identity.

Scheme 3. Proposed catalytic cycle for the teransesterification of esters with ethanol Mo@C.

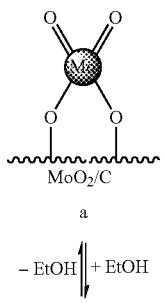

-continued

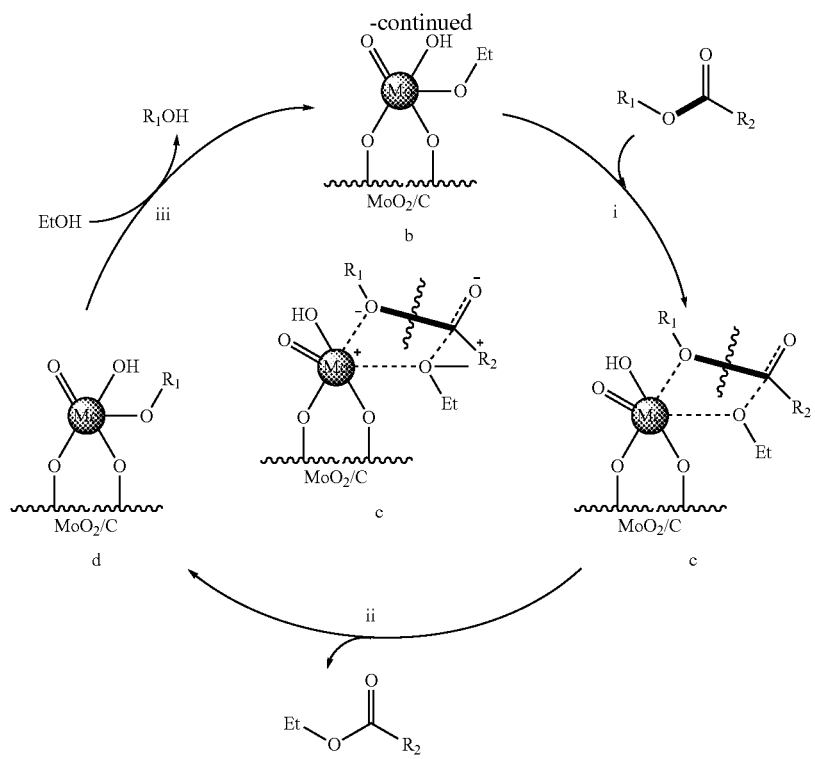

Catalyst Reactivity.

The supported Mo@C catalyst exhibits high activity for the production of $H_2$ from MeOH and EtOH. Notably, the catalyst not only tolerates water, but water itself enhances the recyclability of the catalyst. The formaldehyde and acetaldehyde polymer products, whose formation drives the reaction forward, were found to coat or adsorb to the surface of the catalyst and effectively block the Mo active sites from further reacting. The catalyst can be regenerated by simply washing with water at room temperature, or by operating the reaction under hydrous conditions similar to what could be expected in a bio-refinery.

As evidenced above, the supported Mo@C catalyst is highly active for both transesterification and oxidative esterification of aldehydes. Interestingly, reactivity appears to be based on steric effects between the incoming substrate molecule and the catalyst support. There is also evidence of positive adsorption between electron rich aromatic substrates/products and the activated carbon support. Notably, electron rich cinnamaldehyde and para-tolualdehyde do not undergo oxidative transesterification with EtOH (Table 7, entries 3 and 4). Both of these substrates adsorb to the surface (as evidenced by their disappearance by $^1$H NMR spectroscopy with respect to internal standard. Both substrates were recovered unreacted after stirring a suspension of the catalyst in toluene overnight.

EXAMPLES OF THE INVENTION

The following non-limiting examples and data illustrate various aspects and features relating to the compositions and/or methods of the present invention, including the production of hydrogen from bio alcohols, as is available through the synthetic methodology described herein. In comparison with the prior art, the present catalyst compositions and related methods provide results and data which are surprising, unexpected and contrary thereto. While the utility of this invention is illustrated through the use of certain catalyst compositions and support components thereof, alcohols, esters and aldehydes which can be used therewith, it will be understood by those skilled in the art that comparable results are obtainable with various other related compositions and support components, alcohols, esters and aldehydes, as are commensurate with the scope of this invention.

Materials and Methods.

General.

Where specified, air-sensitive manipulations were carried out using standard glovebox and Schlenk line techniques. Anhydrous-grade substrates and n-octane were obtained from commercial vendors and used as received unless otherwise noted. Hydrogen (UHP), nitrogen (UHP), and argon (UHP) were purchased from Airgas. The carbon support was purchased from Strem, sieved to a particle size less than 104 dried at 150° C. for 24 hours and cooled under vacuum prior to supporting reactions. Anhydrous dichloromethane was obtained from commercial vendors and distilled from $CaH_2$ before use. Anhydrous EtOH was obtained from Sigma Aldrich and dried over 3 Å molecular sieves before use. $MoO_2Cl_2$ and dimethoxyethane (anhydrous, 99.5%) were purchased from Sigma-Aldrich and used without further purification. Anhydrous-grade methanol (sure-seal) and toluene were obtained from Sigman-Aldrich and used as received. $D_2O$, $CD_3CD_2OD$, and $CD_3OD$ were purchased from Cambridge Isotopes and used as received. Formalin (37 wt % in $H_2O$), $^{13}CH_3CH_2OH$, $^{13}CH_3OH$, 2,4-dinitrophenylhydrazine (2,4-DNPH), formaldehyde-2,4-DNPH adduct, and acetaldehyde-2,4-DNPH adduct were purchased from Sigma-Aldrich and used as received.

$MoO_2Cl_2$(dme) was prepared as provided below, according to literature precedent, crystallized from a 1:1 dichloromethane/ether mixture, and used without further purification. (See, e.g., Dreisch, K.; Andersson, C.; Sta<<handske, C., Synthesis of $MO_2Cl_2$(N,N,N',N'-tetramethylethylenediamine) (M=Mo and W) and crystal structure of $WO_2Cl_2$(N,N',N'-tetramethylethylenediamine)—an unprecedented coordination geometry in the $WO_2Cl_2$ Core. *Polyhedron* 1992, 11 (17), 2143-2150.) Catalytic reactions were carried out in a HEL SS Cat 7 reactor with cooling reflux head and with 6 10 mL glass vials and PTFE magnetic stir bars allowing up to 6 different separate reactions in the reactor at one time (max pressure: 100 bar). All products were identified by comparison to known spectra.

Physical and Analytical Measurements.

NMR spectra were recorded on a Varian Inova-500 (FT, 500 MHz, $^1$H, 100 MHz, $^{13}$C), a Varian Inova-400 (FT, 400 MHz, $^1$H, 100 MHz, $^{13}$C, 376 MHz, $^{19}$F) or a Mercury-400 (FT, 400 MHz, $^1$H; 100 MHz, $^{13}$C) spectrometer. Chemical shifts (δ) for $^1$H, and $^{13}$C are referenced to internal solvent. GC-MS analysis was performed on a Waters GCT Premier GC-TOF, coupled to an Agilent 7890A GC with DB-5MS (5% phenyl methyl siloxane, 30 m×250 μm×0.25 μm) capillary column and a time-of-flight (TOF) high resolution detector. Physisorption measurements (BET, BJh) were taken using a Micromeritics ASAP 2010 instrument. Temperature-programmed reduction (TPR) experiments were performed with an AMI-200 analyzer. TPR and BET measurements were performed at the Center for Clean Catalysis (CleanCat) at Northwestern. XPS spectra were recorded at the Keck II facility at Northwestern with a Thermo Scientific ESCALAB 250 Xi spectrometer. Powder X-ray diffraction (PXRD) experiments were carried out in the J. B. Cohen facility at Northwestern using a 9 kW Rigaku Dmax diffractometer equipped with a Cu Kα source. ICP analysis was performed at the QBIC facility at Northwestern University with a Thermo iCAP 7600 ICP-OES instrument. The gas phase mass spec used was a Stanford Research Systems Universal Gas Analyzer 100 (UGA-100).

Example 1

Catalyst Preparation.

In a glove box, a Schlenk flask was charged with 0.38 g (1.3 mmol) solid $MoO_2Cl_2$(dme). The flask was removed from the box, attached to a Schlenk line under an $N_2$ atmosphere, and 30 mL of anhydrous dichloromethane were added to it to form a colorless solution. Under $N_2$, the solution was cannulated into a second flask containing 5 g of pre-dried activated carbon. The resulting suspension was stirred gently for 18 hours at room temperature. The supernatant DCM solution was cannula filtered off and the filtrate washed 2× more with anhydrous DCM. The catalyst was then re-suspended in dichloromethane and vacuum filtered under ambient conditions. The catalyst was further dried in vacuo overnight and could be stored under ambient conditions thereafter. Preparation via this method yielded a catalyst with 2.1 wt % Mo, as determined by ICP.

An alternative procedure was attempted to determine the maximum loading of Mo under grafting conditions. The same procedure as above was carried out, but with 0.45 g of $Mo_2Cl_2$(dme) and 0.5 g carbon (nominally, a weight loading of 30 wt % Mo). After isolating and drying the catalyst, ICP indicates the catalyst weight loading to be about 5.0 wt %, indicating that this is the maximum Mo loading achievable under our conditions.

Example 1a

Preparation of $MoO_2Cl_2$(dme).

A suspension of $MoO_2Cl_2$ (11.12 g, 55.8 mmol) in $CH_2Cl_2$ (100 cm$^3$) was cooled to −78° C. and dme (14 cm$^3$) was added dropwise with vigorous stirring. The cooling bath was then removed and stirring was continued until all the solid material had dissolved (approx. 15 min). The solution was then concentrated until a white solid began to precipitate. The addition of ether (70 cm$^3$) and cooling at −30° C. overnight gave white crystals of $MoO_2Cl_2$(dme). Yield 12.00 g, 74.3%.

Example 1c

Preparation of Supported $MoO_x$ Catalysts:

Various other metal oxides and carbon allotropes can be used, for supports, in addition to activated carbon. For instance and without limitation, prior to grafting, commercial γ-$Al_2O_3$ and anatase $TiO_2$ were heated under vacuum at 450° C. for 4 h, while mw-CNTs were heated at 200° C. for 24 h. Supports were subsequently handled under an atmosphere of $N_2$. Grafting of $MoO_x$ was achieved by introducing a 26.3 mM solution of $MoO_2Cl_2$(dme) in $CH_2Cl_2$ in a 0.26 mmol/(g of support) ratio to the desired support while stirring under flow of $N_2$ at room temperature. Suspensions were allowed to stir for 24 h, after which point they were isolated by filtration and washed with 3×50 mL of $CH_2Cl_2$ and dried under vacuum for 24 h. The resulting % (w/w) of Mo as determined by ICP is 0.783%, 1.38%, and 1.75% for γ-$Al_2O_3$, mw-CNTs, and anatase $TiO_2$ supports respectively. All three proved to be reactive for catalytic hydrogen generation from both MeOH and EtOH, whether neat or in $H_2O$, and can be used in accordance with this invention.

Example 2

General Procedure for MS Analysis of Gas-Phase Catalytic Reaction Products

A 50 mL Schlenk flask was charged with 0.030 g of Mo@C (2.1 wt %), 0.8 mL of toluene, and 0.4 mL of either EtOH or MeOH. A reflux condenser was attached with a port to the gas-phase MS. The solution was degassed, placed under Ar(g) and sealed. The port to the MS was opened, and while stirring at 500 rpm, the flask was lowered into a 90, 60, or 40° C. sand bath.

Example 2A

MS analysis of gaseous products of reactions in neat alcohol or alcohol/$H_2O$ solutions: The same set up was used with 0.030 g Mo@C and 1.0 mL of either neat alcohol or 9:1 $H_2O$:ROH.

Example 2b

MS Analysis of Gaseous Products of Reactions with $D_2O$:
The same set-up was used with 0.030 g Mo@C and 1.0 mL of $D_2O$.

Example 2c

MS analysis of gaseous products of reactions with no solvent: The same set-up was used with 0.030 g of Mo@C.

Example 3

J-Young NMR Tube Experiments:
To a J-young NMR tube, 0.015 g of Mo@C, 0.2 mL of EtOD-$d_6$ or MeOD-$d_4$ and 0.4 mL toluene-$d_8$ were added, and the tube was freeze-thaw degassed and placed under Ar. The tube was then heated in a 90° C. oil bath for 16 h. Note: This reaction only reaches ~1-5% conversion due to the system being closed.

Example 4

General Set-Up for Semi-Batch Reactions:

A 250 mL 3-neck round bottom flask was charged with a magnetic stir bar and a special reflux condenser was attached that contained an adjustable gas inlet sparger inside. Gas flowed down the inside of the tube to the sparger at the end of the tube, near the reaction zone. The gas outlet was at the top of the reflux condenser which led to a T-joint connected to the MS and an outlet vent.

Example 5

Figure 20:
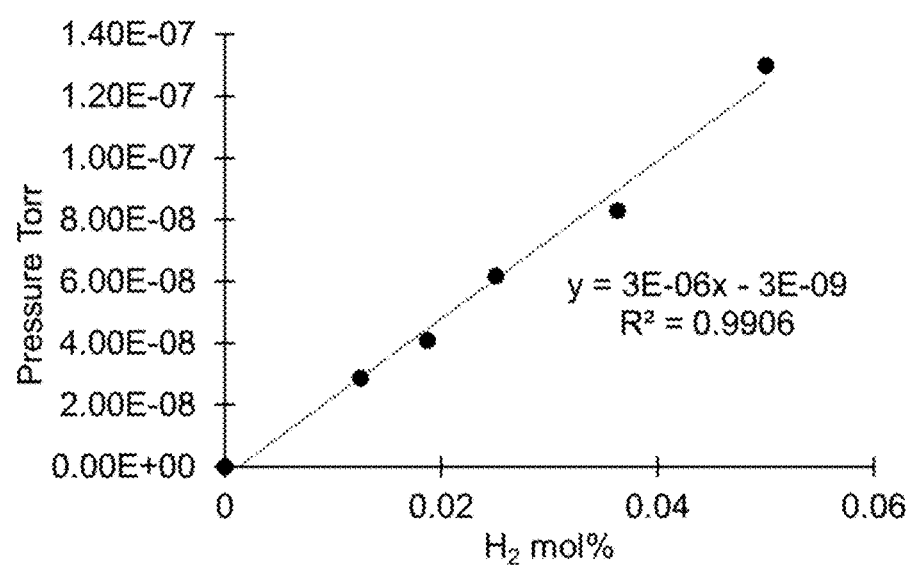
FIG. 20. $H_2$ calibration curve for 1 mL/s gas flow.

Procedures for $H_2$ Quantification Using MS:

Ar(g) and 5% $H_2/N_2$ tanks were connected to mass flow controllers then to the gas inlet of the reactor. The $H_2$ pressure response was monitored by varying the total $H_2$ content in the gas stream while maintaining the same total flow rate (Table 9). A calibration curve relating mol % $H_2$ to pressure response of $H_2$ was obtained at a set gas flow rate (FIG. 20). The most linear response rate was obtained for a flow of 1.0 mL/s.

TABLE 9

$H_2$ calibration of gas phase MS under semi-batch conditions. (Total flow = 1 mL/s gas)

| 5% $H_2/N_2$:Ar | mol % $H_2$ | Pressure ($H_2$) Torr |
|---|---|---|
| 0:100 | 0 | $2 \times 10^{-10}$ |
| 25:75 | 0.0125 | $2.88 \times 10^{-8}$ |
| 37.5:62.5 | 0.0187 | $4.1 \times 10^{-8}$ |
| 50:50 | 0.025 | $6.2 \times 10^{-8}$ |
| 75:25 | 0.0363 | $8.3 \times 10^{-8}$ |
| 100:0 | 0.05 | $1.3 \times 10^{-7}$ |

Example 6

Determination of TOF's:

In a typical experiment, the Ar(g) flow was set to 1 mL/s. The appropriate amount of Mo@C was charged in the flask with a magnetic stir bar and sealed with a septum. The flask was next heated in a 90° C. oil bath, and the alcohol (either neat or in $H_2O$) was added via syringe in a single portion. The pressure response was then recorded, and the $H_2$ conversion determined by taking the $H_2$ produced (in units of total pressure, Torr) and converting to mol % $H_2$ using the calibration curve (FIG. 20). Knowing the total gas flow (1 mL/s), the total moles in a time period could be determined. For repeated additions over 5 days to determine the catalyst stability, 2.0 mL of $H_2O$ was added to the flask and 0.6 mL MeOH was injected at predetermined time points (See Table 3).

Figure 25:
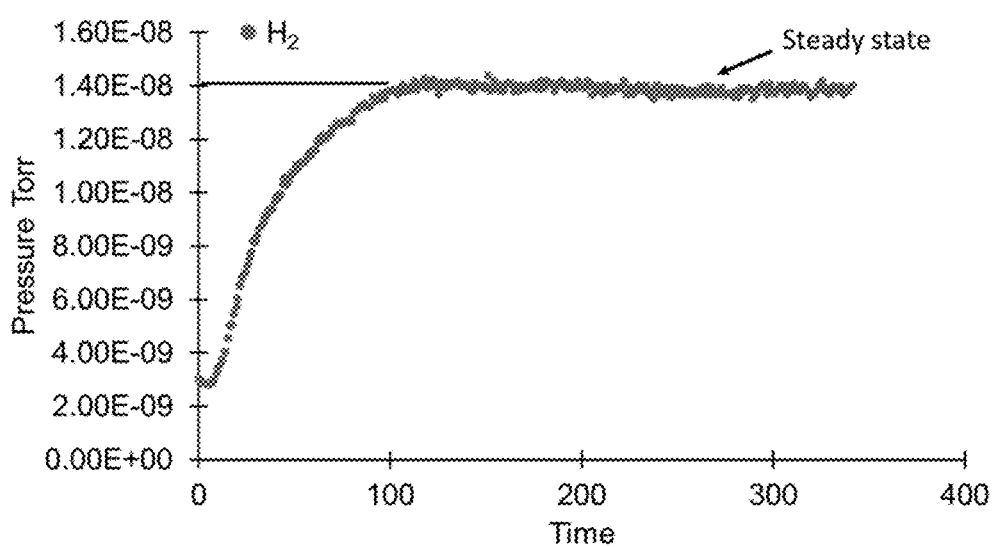
FIG. 25. Example Graph to determine steady state TOF's (line=steady state pressure of $H_2$)

Example TOF Determination:

For data in FIG. 25:
Calibration curve: Pressure (Torr, $H_2$)=$2.556 \times 10^{-6}$ (mol % $H_2$)–$3 \times 10^{-9}$
Total gas flow: $3.976 \times 10^{-5}$ mol/s
Total mol $H_2$ possible (1 mL MeOH): 0.02466 mol
mol Mo (30 mg of 2.1 wt % catalyst): $6.29 \times 10^{-6}$ mol.
Take the pressure (Torr) at steady state and convert to mol % $H_2$ using the calibration curve.
Mol % $H_2$ at steady state=0.889 mol %
Moles/s of $H_2$ at steady state (calculated using total gas flow): $3.578 \times 10^{-7}$ mol/s
TOF=[rate/mol catalyst]=[($3.578 \times 10^{-7}$ mol/s)*(3600 s/h)]/$6.29 \times 10^{-6}$ mol
TOF=205 $h^{-1}$.

Example 7

Procedure for $H_2$ Yield Determination:

To a 25 mL round-bottom flask attached to a reflux condenser with a tube leading to an inverted 50 mL volumetric flask filled with water in a beaker (total water volume≤125 mL), was added 0.0075 g Mo@C, ROH (50 μl EtOH or 32 μl MeOH), the appropriate quantity of $H_2O$, and a magnetic stir bar. The reaction flask was next lowered into a 90° C. bath stirring at 500 rpm and the evolved $H_2$ collected in the graduated cylinder.

Example Calculation of $H_2$ Yield (Table 10 Trial 1, 32 μL of MeOH, 0.791 mmol):
(T) Temperature of $H_2O$: 25° C.=298.15 K
Vapor pressure $H_2O$ (@ 25° C.): 3173.1 Pa
Atmospheric pressure in Chicago (O'Hare): 102298.3 Pa
(P) Pressure difference: 99125.2 Pa=0.978 atm
Volume of $H_2O$: 100 mL
(V) Total Volume of $H_2$ collected: 17 mL
n(moles)=P.V/RT (ideal gas law, R=0.08206 L.atm.mol$^{-1}$.K$^{-1}$)

$$n = \frac{(0.978 \text{ atm})(0.017 \text{ L})}{(0.08206 \text{ L} \cdot \text{atm} \cdot \text{mol}^{-1} \cdot \text{K}^{-1})(298.15 \text{ K})}$$

Moles of $H_2$ collected (n)=0.00068 moles
The number of moles of $H_2$ in water was calculated using Henry's constant ($H_2$ solubility in water) assuming the displaced water was under 1 atm of $H_2$ inside the burette.
Moles of $H_2$ dissolved in 100 mL $H_2O$ at 25° C.: 0.00008 moles $$\text{Yield} = \frac{0.00068 + 0.00008}{0.00091} \times 100\%$$

Yield = 96%.

TABLE 10

$H_2$ Yields at 90° C., stirring at 500 rpm, 32 μL MeOH or 50 μL EtOH with $H_2O$ and Mo@C (0.0075 g).

| System | $H_2$ Yields (%) | Average $H_2$ Yield (%) |
|---|---|---|
| Neat MeOH | Trial 1: 96% | 91 ± 5% |
| | Trial 2: 86% | |
| 6:4 MeOH:$H_2O$ | Trial 1: 91% | 91 ± 1% |
| | Trial 2: 90.5% | |
| 1:9 MeOH:$H_2O$ | Trial 1: 88% | 87 ± 2% |
| | Trial 2: 85% | |
| Neat EtOH | Trial 1: 100% | 100 ± 2% |
| | Trial 2: 102% | |
| 6:4 EtOH:$H_2O$ | Trial 1: 95% | 91 ± 4% |
| | Trial 2: 87% | |
| 1:9 EtOH:$H_2O$ | Trial 1: 90% | 89 ± 2% |
| | Trial 2: 87% | |

Example 8

Procedure for Determining Aldehyde Adsorption on Activated Carbon. Formaldehyde:

A solution of 1 wt % formaldehyde was prepared by dissolving 0.020 g of solid paraformaldehyde (Sigma-Aldrich) in 1.98 g of $D_2O$ (Cambridge Isotopes). To this was added 0.1 mL t-butanol (Sigma-Aldrich, dried over 4A molecular sieves) as an internal $^1$H NMR standard. A similar procedure was followed with acetaldehyde (Sigma-Aldrich). To 1.0 mL of 1.0 wt % aldehyde solution was added 10 mg of activated carbon. The mixture was stirred for 30 min before filtration. Disappearance of aldehyde in the supernatant was quantified by inverse-gated decoupling $^{13}$C NMR using the tert-butanol signal at δ 29.5 ppm as internal standard.

Example 9

Acetaldehyde:
A solution of 1.0 wt % acetaldehyde was prepared by dissolving 0.020 g of solid acetaldehyde (Sigma-Aldrich) in 1.98 g of $D_2O$ (Cambridge Isotopes). To this was added 0.1 mL tert-butanol (Sigma-Aldrich, dried over 4A molecular sieves) as an internal standard. To 1.0 mL of 1 wt % aldehyde solution was added 10 mg of activated carbon. The mixture was stirred for 30 minutes before being filtered. Disappearance of aldehyde was monitored by inverse-gated decoupling $^{13}$C NMR using the tert-butanol signal at 29.5 ppm as internal standard.

Example 10

Procedure for Collecting Evolved Formaldehyde Gas in Toluene-$d_8$:
A 25 mL round-bottom flask attached to a reflux condenser fitted with a rubber septum and cannula was charged with MeOH (3.0 mL), $D_2O$ (1.0 mL), Mo/C (0.015 g), and a magnetic stir bar. The cannula was inserted into a J-young NMR tube with 0.5 mL toluene-$d_8$ fitted with a rubber septum and vent needle, with the tip of the cannula submerged in the toluene-$d_8$. The NMR tube was cooled in a −78° C. cold bath and the round-bottom flask was lowered into a 75° C. heating batch with stirring at 500 rpm. Next, the gas was collected, and the NMR tube was then sealed with a Teflon screw cap and allowed to warm to room temperature, at which time an $^1$H NMR spectrum was taken.

Example 11

Procedure for Quantifying Aldehydes Using 2,4-Dinitrophenylhydrazine:
A 50 mL Schlenk flask was charged with 0.005 g of Mo@C (2.1 wt %), 1.0 mL $H_2O$, and 0.2 mL of either EtOH, MeOH, or 2.0 mL of formalin (37% in $H_2O$). A reflux condenser was attached and the solution was degassed and placed under Ar(g) and sealed. A cannula was inserted at the top of the reflux condense through a septum leading to a solution of Brady's Reagent (below). While stirring at 500 rpm, the flask was lowered into a 90, ° C. oil bath until gas evolution ceased. The solution of Brady's reagent was next extracted with ethyl acetate (5×25 ml), the organic layer washed with $H_2O$ (2×25 mL), dried over $MgSO_4$, and the solvent removed in vacuo to yield the yellow hydrozone solid. The solids were purified by chromatography (ethyl acetate/hexanes on silica) and compared to authentic standards purchased from Sigma-Aldrich. Formalin was used as a control to verify the procedure. Note: Allowing the solutions of aldehyde and Brady's reagent to stand at room temperature for significant periods of time (3-7 days) also resulted in precipitation of the corresponding hydrazone.

Preparation of Brady's Reagent for aldehydes/ketones: (Caution! 2,4-dintrophenylhydrazine is a shock explosive). ~20 g of 2,4-dinitrophenylhydrazine slurried in $H_2O$ was added to a 500 mL Erlenmeyer flask containing 50 mL $H_2O$ using a plastic scoopula. $H_2SO_4$ (35 mL) was added slowly concurrently with 50 mL EtOH. The solution was allowed to stir for 3 h and filtered to remove undissolved reagent. The solution was used directly for aldehyde quantification tests.

Example 12

Figure 21A:
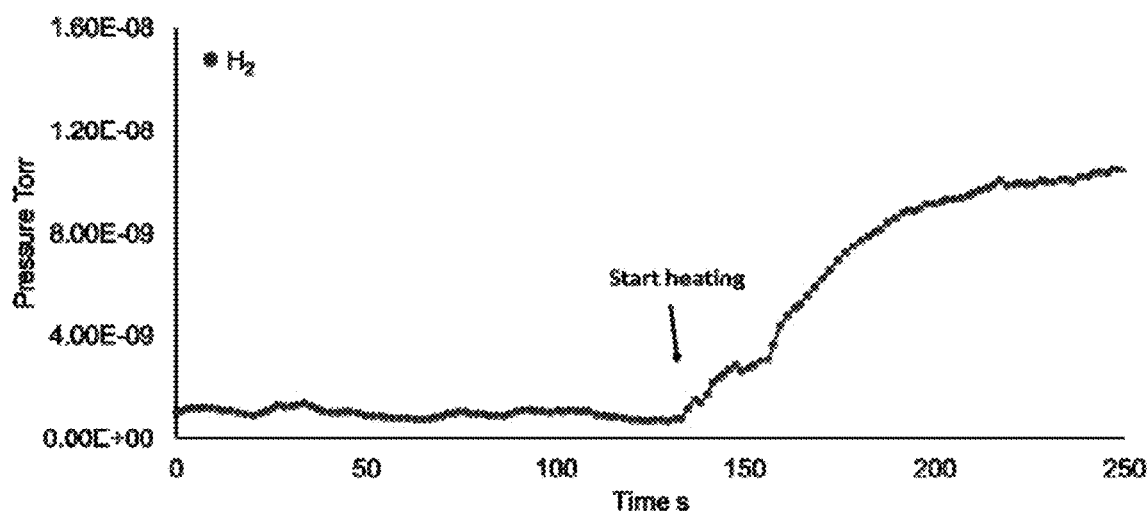
FIGS. 21A-B. Gas phase MS (pressure vs time) traces of successive MeOH additions (1.0 mL, denoted by ø in graph b.) to Mo@C (0.030 g) added before all MeOH is consumed (90° C. and 500 rpm). (A) Shows the point (time ~250 s) when another 1.0 mL portion of MeOH is added. (B) Shows the successive 1.0 mL MeOH additions, ø). Note: formaldehyde not shown.
Figure 21B:
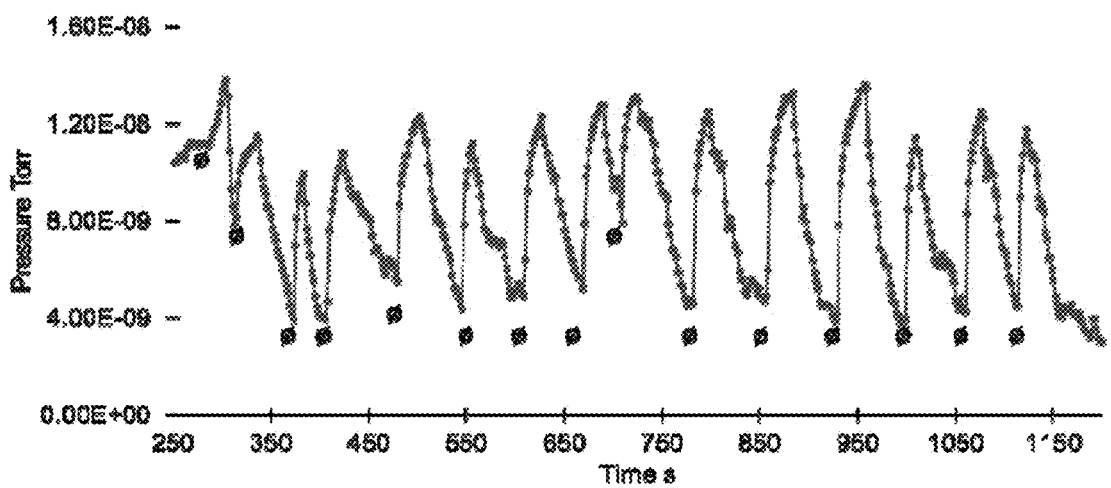

FIG. 21 shows that this catalytic system does not deactivate as long as MeOH remains in the reaction vessel. By adding another 1.0 mL of MeOH at the 250 s mark, catalytic activity is maintained over multiple MeOH addition cycles. It is postulated that the MeOH helps solubilize the formaldehyde oligomers and prevents catalyst coating. This is in marked contrast to FIG. 10, where all MeOH in the system is consumed, and the catalyst gradually deactivates. If the system is left heating for several h, the catalyst completely deactivates and no longer produces $H_2$ on addition of fresh MeOH.

Example 13

Figure 22:
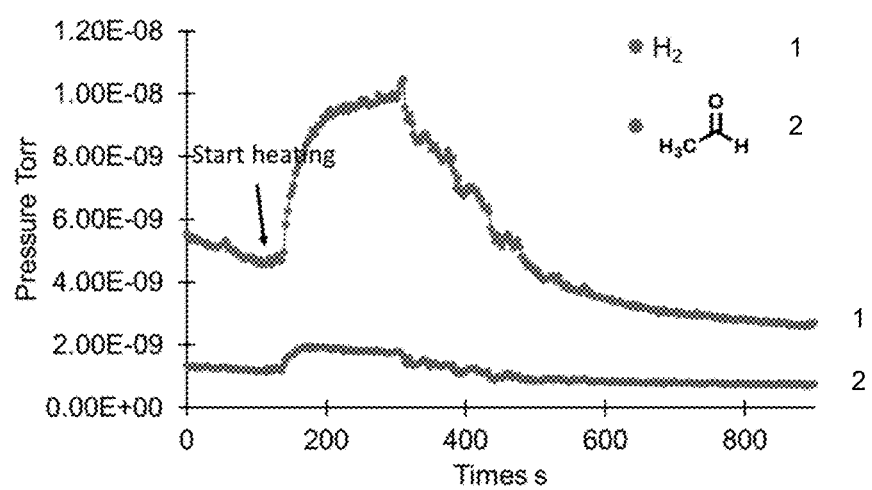
FIG. 22. Gas phase MS (pressure versus time) scan of Mo@C (0.030 g) with EtOH at 90° C. (500 rpm, 0.4 mL EtOH and 0.8 mL toluene).

FIG. 22 shows the production of $H_2$ from EtOH. Acetaldehyde and $CO_2$ have the same mass of m/z=44, so it cannot be determined explicitly that $CO_2$ is not produced, however, based on the lack of $CO_2$ observed in the reaction with MeOH, it is concluded that $CO_2$ is unlikely to form in the reaction with EtOH. After a period of 4 h (not shown), another aliquot of EtOH (0.4 mL) was added to this reaction mixture and no $H_2$ was produced, indicating the catalyst had deactivated.

Example 14

Figure 4A:
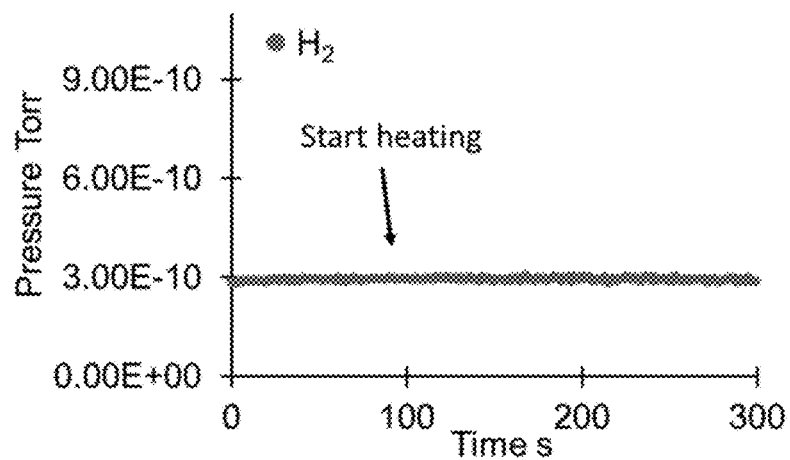
FIGS. 4A-D. Control experiments at 90° C. and stirring at 500 rpm. (A) Mo@C (0.030 g) with no alcohol. (B) $H_2O$ (1.0 mL) and Mo@C (0.030 g). (C) Experiments with $MoO_3$ (0.0013 g, 9 μmol) and 1.0 mL EtOH. (D) Experiments with the activated carbon support (0.030 g) and 1.0 mL EtOH. Note: acetaldehyde not shown.
Figure 4B:
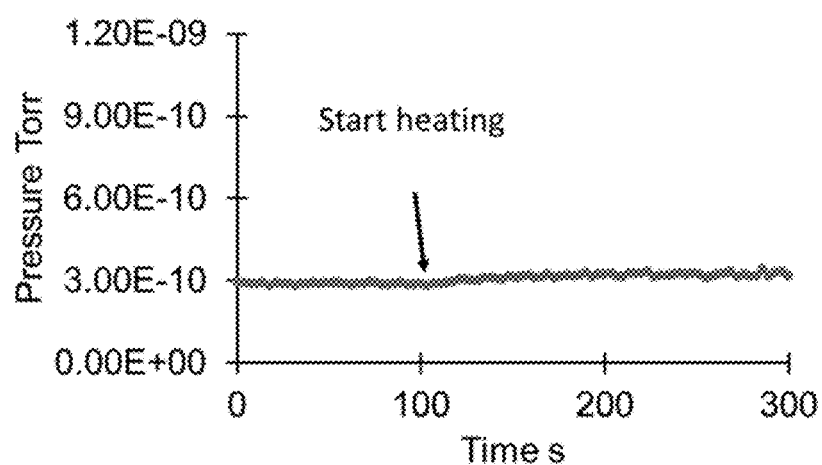
Figure 4C:
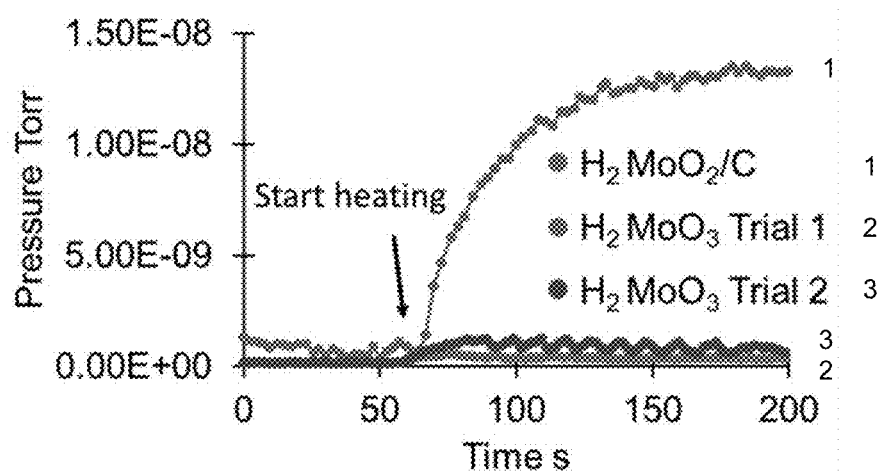
Figure 4D:
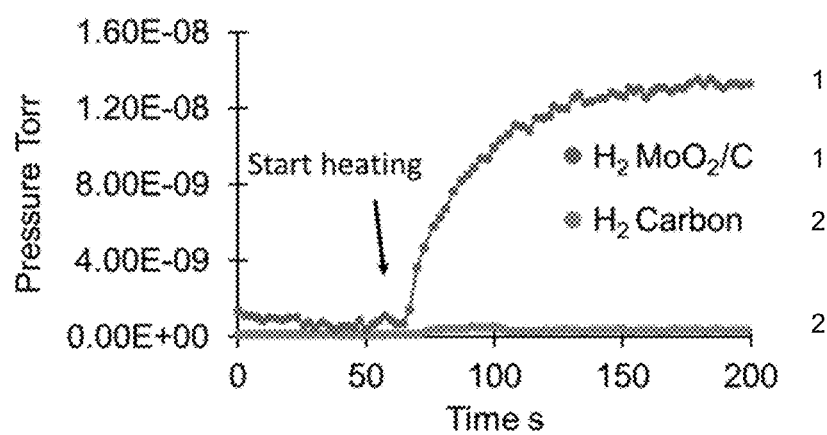

FIGS. 4A-D show the control experiments. FIG. 4A shows that no $H_2$ is produced when heating the catalyst without alcohol. FIG. 4B shows that no $H_2$ is produced from $H_2O$. FIG. 4C shows the reaction of commercially available $MoO_3$ (9 mmol) with EtOH. For comparison, a plot of $H_2$ production using Mo@C (6.3 μmol Mo) is shown as well. FIG. 4D shows the reaction of activated carbon with EtOH, and includes a comparison plot when using Mo@C.

Example 15

Figure 5:
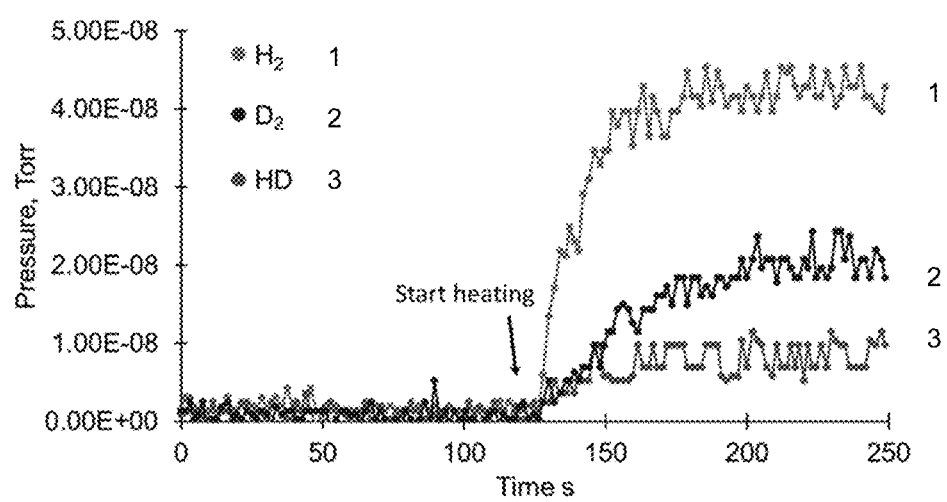
FIG. 5. Gas phase MS (pressure vs time) trace of Mo@C (0.030 g) with MeOD-$d_4$ at 90° C. (500 rpm, 0.40 mL MeOD-$d_4$ and 0.80 mL toluene). Note: formaldehyde not shown.
Figure 6:
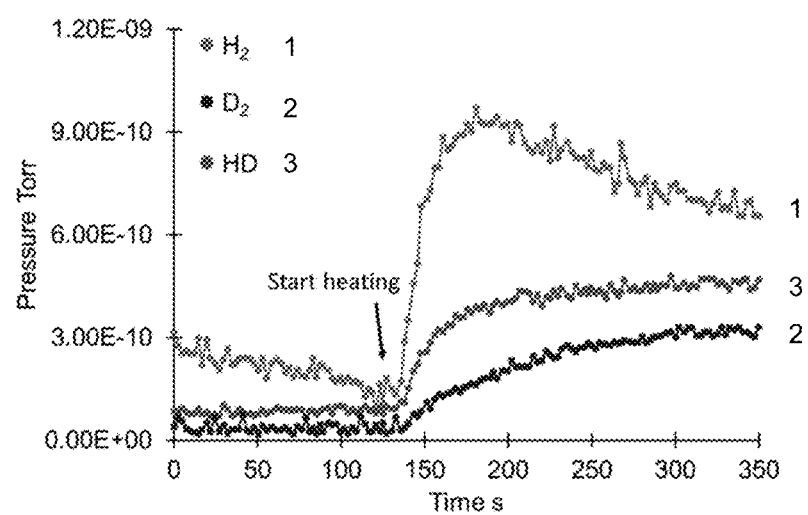
FIG. 6. Gas phase MS (pressure vs time) trace of Mo@C (0.030 g) with EtOD-$d_6$ at 90° C. (500 rpm, 0.40 mL EtOD-$d_6$ and 0.80 mL toluene). Note: acetaldehyde not shown.
Figure 7A:
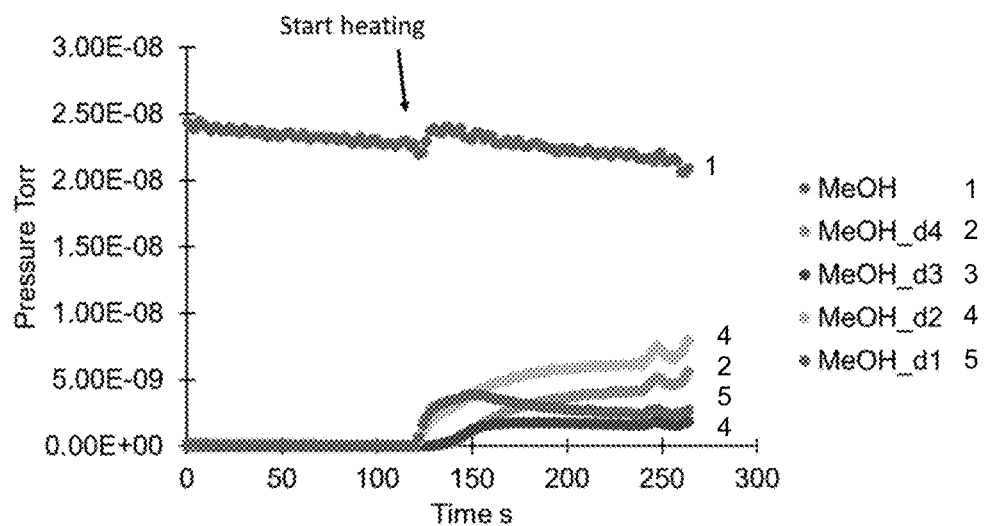
FIGS. 7A-B. Gas phase MS (pressure vs time) trace. A. Freshly opened ampule of 1 mL MeOD-$d_4$ at 90° C. B. 1 mL of EtOD-$d_6$ (from a 10 mL bottle) at 90° C.
Figure 7B:
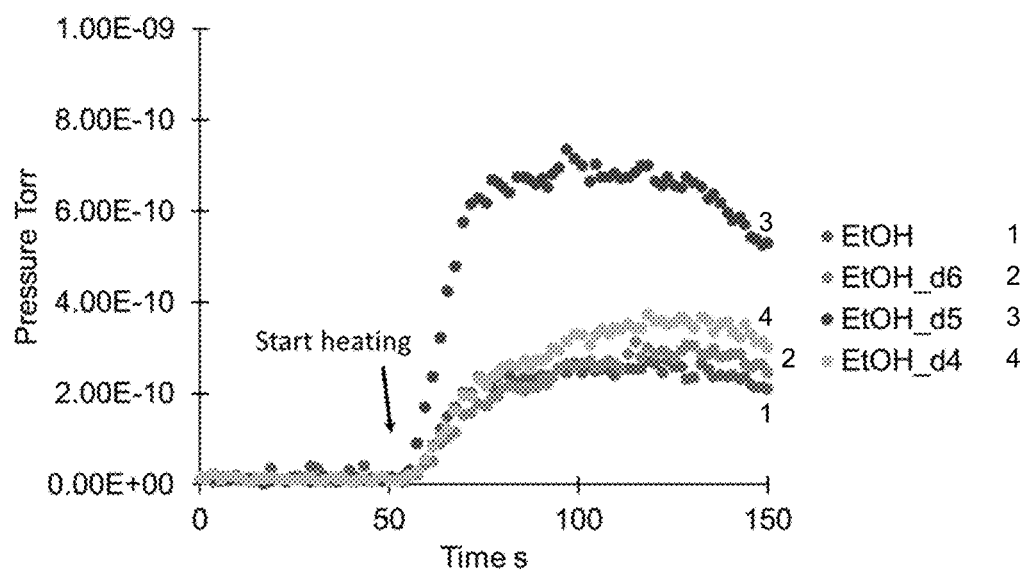
Figure 8:
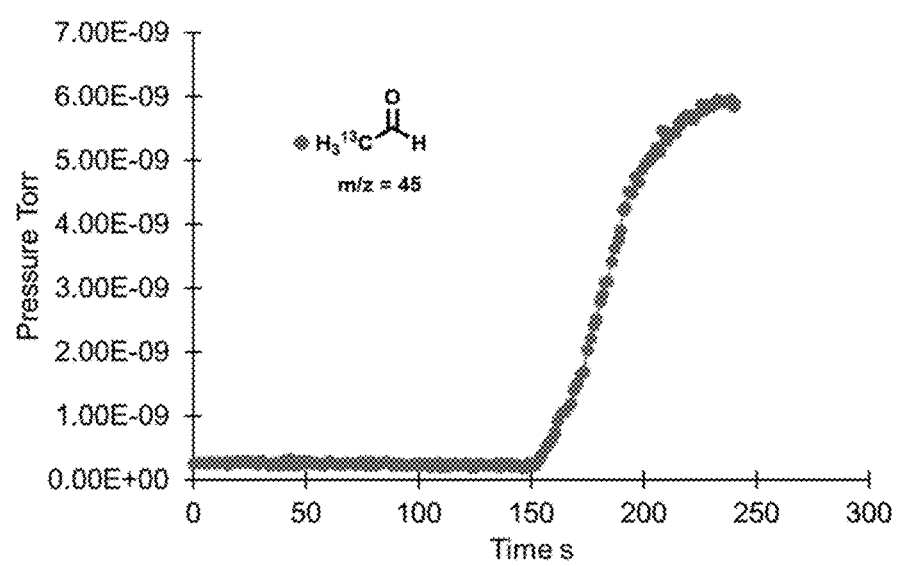
FIG. 8. Gas Phase MS (pressure vs time) trace of Mo@C (0.030 g) with $^{13}CH_3CH_2OH$ at 90° C. (500 rpm, start heating at 150 seconds). Note: $H_2$ not shown.
Figure 9:
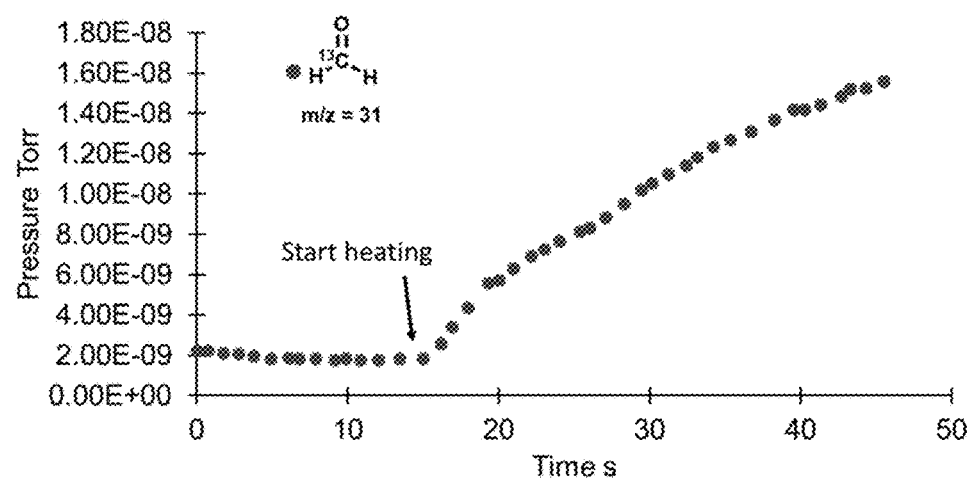
FIG. 9. Gas Phase MS (pressure vs time) trace of Mo@C (0.030 g) with $^{13}CH_3OH$ at 90° C. (500 rpm). Note: $H_2$ not shown.

FIGS. 5 and 6 show the reactions with MeOD-$d_4$ and EtOD-$d_6$, respectively. The presence of some $H_2$ and HD is detected in both samples, indicating that there is a source of protons in the system. To determine if the source is the activated carbon support, MeOD-$d_4$ was taken up with Mo@C in dry toluene-$d_8$ in a sealed J-young NMR tube and heated to 90° C. The $^1$NMR spectrum (not shown) shows the presence of $H_2$ as well as $H_2O$, which likely desorbed from the support. The gas phase MS (pressure vs time) of the deuterated alcohols MeOD-$d_4$ and EtOD-$d_6$ directly from Cambridge Isotopes were taken to determine if the reagents themselves were also sources of protons and their spectra are shown in FIG. 7. As seen in FIG. 7, the deuterated reagents also contain significant quantities of protons which could also be a source of HD and $H_2$. Alternatively, the mass spec rapidly scrambles H and D with protic sources in the instrument, which has been observed previously in the literature.

Example 16

Figure 23:
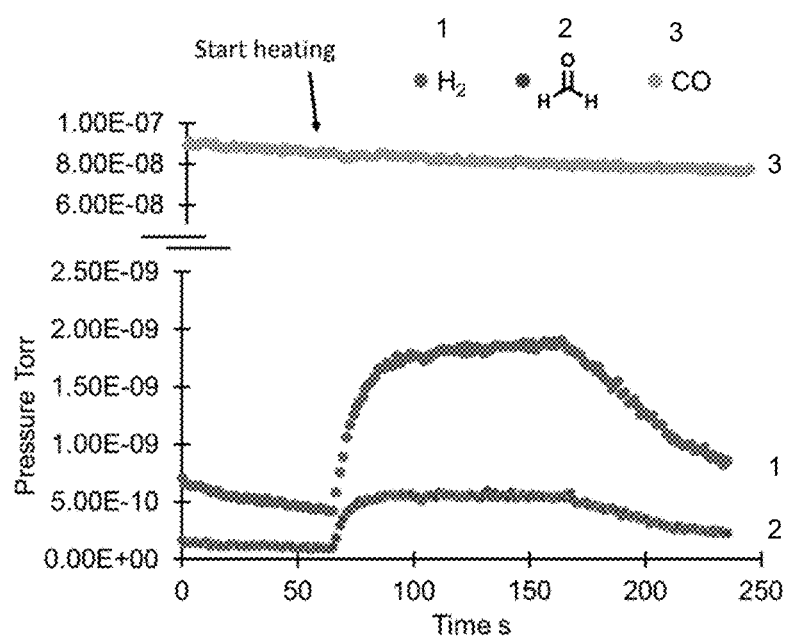
FIG. 23. Gas phase MS (pressure vs time) trace of Mo@C (0.030 g) with MeOH at 90° C. (500 rpm, 1.0 mL MeOH) showing no CO production.
Figure 24:
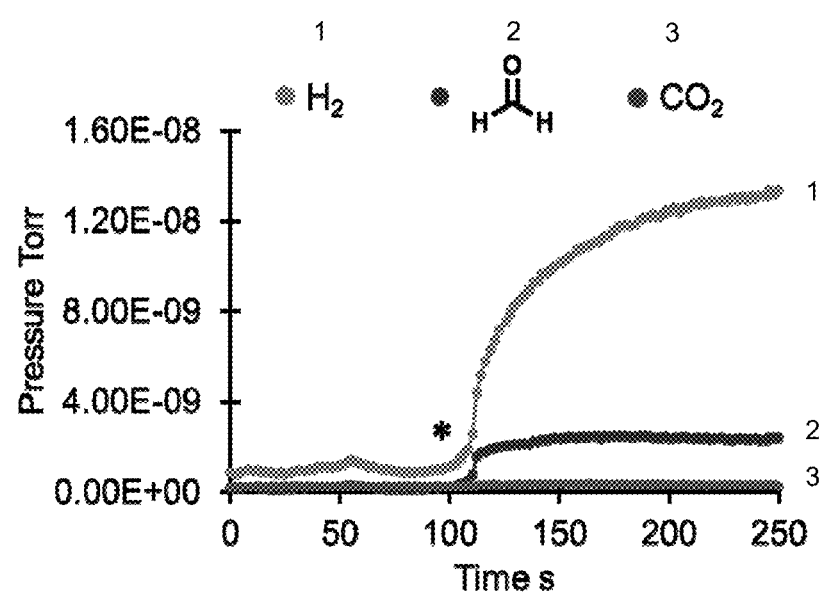
FIG. 24. Gas phase MS pressure versus time scan of the reaction of Mo@C (0.030 g) with MeOH at 90° C. (500 rpm, 0.4 mL EtOH and 0.8 mL toluene). No $CO_2$ is evolved. *=heating start.

Based on the lack of CO (FIG. 23) and $CO_2$ (FIG. 24) produced in the reaction and the yields of 1 eq. of $H_2$ near 100%, it is proposed that the oligomeric and monomeric aldehydes are formed nearly quantitatively. For both MeOH and EtOH, the product oligomeric and monomeric aldehydes either adsorb onto the catalyst surface and/or are released into the gas phase (as monomers) as evidenced by gas-phase MS, chemical titration, and NMR spectroscopy.

Example 17

General Procedures for Transesterification Catalytic Runs.

A 10 mL vial was charged with a magnetic stirbar, Mo/C catalyst, substrate, mesitylene internal standard and anhydrous EtOH (amounts subject to specific conditions). A small portion of the solution (<0.05 mL) was removed and added to 0.4 mL CDCl$_3$ for $^1$H NMR spectroscopy at time zero. The vials were then placed into the SS cat 7 reactor with PTFE cold finger seals to prevent cross contamination, the reactor sealed, and was purged to 200 psi 5 times before pressurizing to 200 psi with Ar(g). Cold tap water was run through the cooling reflux head and the reactor was heated to the desired temperature. After a specific time, the reactor was cooled to room temperature (25° C.) and depressurized. A small portion of the solution (<0.05 mL) was removed and added to 0.4 mL CDCl$_3$ for $^1$H NMR and GC-MS analysis. Conversion was determined from the consumption of starting substrate to mesitylene internal standard by $^1$H NMR. Product yields were determined from product signals versus mesitylene internal standard by $^1$H NMR. GC-MS was utilized for confirmation of all products present, but not for quantitation.

Example 18

Procedure for Determining the Order in EtOH.

Four 10 mL vials were each charged with n-octyl acetate (0.2 mL, 1 mmol), Mo/C (2.1 wt %, 0.0457 g, 1 mol % Mo), mesitylene (0.14 mL), 2 mL of anhydrous octane, and a PTFE coated magnetic stir bar. 1, 2, 3, and 4 molar equivalents of EtOH (relative to substrate) was added via syringe to each vial. The vials were then placed into the SS cat 7 reactor with PTFE cold finger seals to prevent cross contamination, the reactor sealed, and was purged to 200 psi 5 times before pressurizing to 200 psi with Ar(g). Cold tap water was run through the cooling reflux head and the reactor was heated to 90° C. for 3 hours. The reactor was cooled to room temperature (25° C.) and depressurized. A small portion of the solution (<0.05 mL) was removed and added to 0.4 mL CDCl$_3$ for $^1$H NMR analysis. Conversion was determined from the consumption of starting substrate to mesitylene internal standard by $^1$H NMR.

Example 19

Procedure for Determining the Order in Mo.

Four 10 mL vials were each charged with n-octyl acetate (0.2 mL, 1 mmol), mesitylene (0.14 mL), 2 mL anhydrous EtOH, and a PTFE coated magnetic stir bar. Different amounts of Mo/C were added to each vial (2.1 wt %, 0.0457 g, 1 mol % Mo, 0.0686 g, 1.5 mol % Mo, 0.0914 g, 2 mol % Mo, and 0.1371 g, 3 mol % Mo). The vials were then placed into the SS cat 7 reactor with PTFE cold finger seals to prevent cross contamination, the reactor sealed, and was purged to 200 psi 5 times before pressurizing to 200 psi with Ar(g). Cold tap water was run through the cooling reflux head and the reactor was heated to 90° C. for 1 hour. The reactor was cooled to room temperature (25° C.) and depressurized. A small portion of the solution (<0.05 mL) was removed and added to 0.4 mL CDCl$_3$ for $^1$H NMR analysis. Conversion was determined from the consumption of starting substrate to mesitylene internal standard by $^1$H NMR.

Example 20

Procedure for Eyring Analysis (*Minimum of 3 Runs Per Temperature).

Three 10 mL vials were each charged with n-octyl acetate (0.2 mL, 1 mmol), Mo/C (2.1 wt %, 0.0457 g, 1 mol % Mo), mesitylene (0.14 mL), 2 mL of anhydrous EtOH, and a PTFE coated magnetic stir bar. The vials were then placed into the SS cat 7 reactor with PTFE cold finger seals to prevent cross contamination, the reactor sealed, and was purged to 200 psi 5 times before pressurizing to 200 psi with Ar(g). Cold tap water was run through the cooling reflux head and the reactor was heated to the desired temperature for a set amount of time. The reactor was cooled to room temperature (25° C.) and depressurized. A small portion of the solution (<0.05 mL) was removed and added to 0.4 mL CDCl$_3$ for $^1$H NMR analysis. Conversion was determined from the consumption of starting substrate to mesitylene internal standard by $^1$H NMR. (90° C. runs for 1 hour, 80° C. run for 2 hours, 70 and 60° C. were run for 6 hours respectively).

Example 21

Procedure for Testing Catalyst Recyclability.

A 10 mL vial was charged with n-octyl acetate (0.4 mL, 2 mmol), mesitylene (0.14 mL), Mo/C (2.1 wt %, 0.0914 g, 1 mol % Mo) and 4 mL of anhydrous EtOH with a PTFE coated magnetic stir bar. The vial was then placed into the SS cat 7 reactor with a PTFE cold finger seal to prevent cross contamination, the reactor sealed, and was purged to 200 psi 5 times before pressurizing to 200 psi with Ar(g). Cold tap water was run through the cooling reflux head and the reactor was heated to 90° C. for 1 hour. The reactor was cooled to room temperature (25° C.) and depressurized. A small portion of the solution (<0.05 mL) was removed and added to 0.4 mL CDCl$_3$ for $^1$H NMR analysis. Conversion was determined from the consumption of starting substrate to mesitylene internal standard by $^1$H NMR. The remaining solution was filtered using a Buchner funnel and the Mo/C catalyst was collected and air dried on the filter paper. The catalyst was collected (0.0713 g, theoretical mmol of 0.0161 if still 2.1 wt %), and was used again with n-octyl acetate (0.32 mL, 1.61 mmol), mesitylene (0.14 mL) and 3.2 mL EtOH under the same conditions. The catalyst was filtered and collected (0.0700 g, theoretical mmol of 0.0153 if still 2.1 wt % Mo), and was used again with n-octyl acetate (0.30 mL), mesitylene (0.14 mL), and 3 mL EtOH under the same conditions.

Example 22

Procedure for Hot Filtration Test.

Mo/C (2.1 wt % 0.0457 g) was added to 6 mL of anhydrous EtOH under nitrogen and sealed in a Schlenk flask. The solution was heated to 60° C. for 4 hours, then filtered hot using a cannula filter into another Schlenk flask under nitrogen. After cooling, this solution was added to a 10 mL vial along with n-octyl acetate (0.2 mL, 1 mmol), mesitylene (0.14 mL) and a PTFE coated magnetic stir bar. The vial was then placed into the SS cat 7 reactor with a PTFE cold finger seal to prevent cross contamination, the reactor sealed, and was purged to 200 psi 5 times before pressurizing to 200 psi with Ar(g). Cold tap water was run through the cooling reflux head and the reactor was heated to 90° C. for 1 hour. The reactor was cooled to room temperature (25° C.) and depressurized. A small portion of the solution (<0.05 mL) was removed and added to 0.4 mL CDCl₃ for ¹H NMR analysis. Conversion was determined from the consumption of starting substrate to mesitylene internal standard by ¹H NMR.

Example 23

XPS Measurements.

A sample of catalyst powder was packed tightly onto double-sided copper tape attached to a stainless steel sample tray. The sample tray was outgassed in the sample entry chamber until a vacuum of at least $2\times10^{-5}$ Torr was obtained, typically for 30 min. The sample tray was then admitted to the UHV chamber and the electron flood gun turned on to compensate for charge. The sample was further allowed to outgas in the UHV chamber until stable vacuum was obtained, typically on the order of $8\times10^{-8}$ Torr. Spectra were measured in the CAE mode with ten to fifty scans apiece at a pass energy of 20 eV and a dwell time of 50 ms. The resulting spectra were smoothed and peak-fitted according to standard software techniques. No species other than C, O, and Mo were detected on the catalyst surface, suggesting that impurities detected by ICP are in the bulk. To compensate for charging effects the binding energies of all observed peaks were corrected by setting the adventitious carbon peak equal to 285.0 eV.

Example 24

TPR Measurements.

In a quartz U-tube, 180 mg of catalyst was loaded atop a packed bed of quartz wool. The U-tube was affixed to the gas line in a heated reactor. A thermocouple probe was fixed inside the U-tube so that it came into contact with the top of the catalyst powder. The catalyst was heated to 550° C. at a rate of 10° C./min under a flow of 5% hydrogen in nitrogen at 30 sccm.

Example 25

Procedure for Error Analysis

The errors reported for activation parameters were determined using Regression Analysis workbook in Excel (Rodney Carr, Deakin University, Australia and Neville hunt, Coventry University, UK as part of the OATBRAN project). All data is reported at the 95% confidence interval.

Example 26

To extend the study summarized in Table 4, transesterification in the presence of H₂O (0 to 1 equiv) did not diminish the catalytic activity at 90° C., indicating the Mo@C catalyst is not poisoned under these conditions. No reaction occurs in the absence of catalyst or with the activated carbon support alone (Table 11, entries 1 and 2). In a control study with n-octyl acetate at 90° C. in dry EtOH, MoO₃ is found to exhibit some activity; however, under the same conditions, the yield (mmol product/mol Mo h⁻¹) is 5.8× higher for Mo@C, confirming the high activity of the carbon-supported dioxo-Mo species.

TABLE 11

Acetate Transesterification Substrate Scope[a]

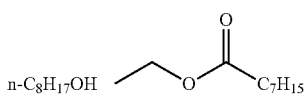

| | Substrates, 1 | Products, 2/3 | Time (h) | Conv. (Yield) % |
|---|---|---|---|---|
| 1[b] | n-C₈H₁₇OAc | n-C₈H₁₇OH | 2 | 0 |
| 2[c] | n-C₈H₁₇OAc | n-C₈H₁₇OH | 2 | 0 |
| 3[d] | n-C₈H₁₇OAc | n-C₈H₁₇OH | 2 | 66 (—) |
| 4 | n-C₈H₁₇OAc | n-C₈H₁₇OH | 1 | 17 (20) |
| | | | 16 | 99 (96) |
| 5 | n-C₈H₁₇OC(O)C₇H₁₅ | n-C₈H₁₇OH 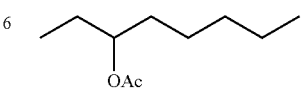 | 16 | 43 (2, 43) (3, 40) |
| 6 | 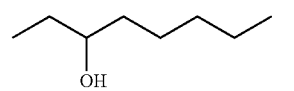 OAc | 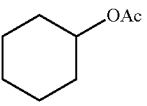 OH | 16 | 47 (44) |
| 7 | 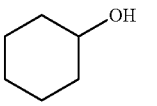 OAc | 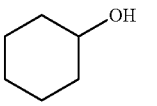 OH | 16 | 54 (49) |

TABLE 11-continued

Acetate Transesterification Substrate Scope[a]

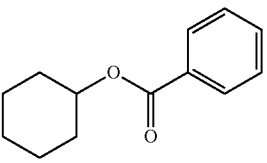 [SMILES: O=C(OC1CCCCC1)c1ccccc1]

| Substrates, 1 | Products, 2/3 | Time (h) | Conv. (Yield) % |
|---|---|---|---|
| 8 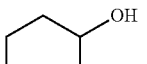 | 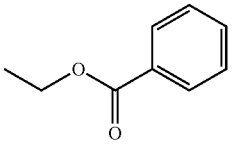 | 16 | 76 (2, 25) (3, 30) |
| 9 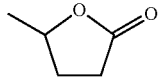 | 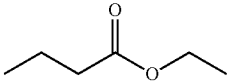 | 16 | 25 (25) |
| 10 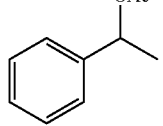 | 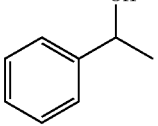 | 16 | 44 (2, 14) (C=O, 8) |
| 11 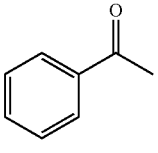 | 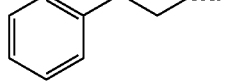 | 16 | 99 (77) |
| 12 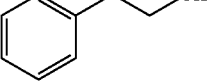 | 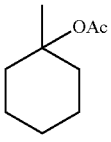 | 16 | 97 (97) |
| 13 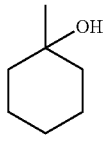 R = C(O)C$_7$H$_{15}$ | R = C(O)C$_7$H$_{15}$ 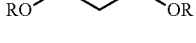  | 2 | 80 (17) (66) |

[a]Conditions: 1 mmol substrate, 1 mol % Mo (0.046 g of 2.1 wt % Mo@C), 2 mL dry EtOH, 200 psi, Ar$_{(g)}$, 500 rpm, conversion and yields determined by reference to mesitylene internal standard by $^1$H NMR spectoscopy; products were also confirmed by GC-MS analysis but not quantified by this method. Acetaldehyde diethyl acetal was observed for reactions with an —OAc group by $^1$H NMR but were not quantified.
[b]no catalyst.
[c]0.0475 g of activated charcoal as catalyst.
[d]10 mol % MoO$_3$ as catalyst.

As demonstrated, the present invention provides a new supported molybdenum oxo catalyst that shows high activity for the hydrogen liberation from lower alcohols, transesterification, and the oxidative esterification of aldehydes at mild temperatures (e.g., <~90° C.) and pressures (e.g., ~1 to 200 psi).

While the principles of this invention have been described in conjunction with specific embodiments, it should be understood clearly that these descriptions are added only by way of example and are not intended to limit, in any way, the scope of this invention. For instance, the present invention can be directed to methodologies and associated catalytic compositions wherein a support component can be selected from various other carbon-based materials including but not limited to graphite, carbon black, activated carbon fibers, carbon-covered alumina, graphite intercalation compounds, glassy carbon, pyrolytic carbon, polymer-derived carbon, fullerenes and carbon nanotubes. Likewise, such methodologies and catalytic compositions can comprise a support selected from various oxides including but not limited to silica, dehydroxylated alumina, sulfated zirconia, zirconia, iron oxide, ceria, hafnia, and magnesium oxide.

We claim:

1. A composition comprising a molybdenum dioxo moiety coupled to a support component comprising an oxygen moiety, said composition absent an $MoO_3$ moiety, the composition having a Mo surface density in the range from 0.10 to 0.22 $Mo/nm^2$.

2. The composition of claim 1 wherein said support component comprises a metal oxide.

3. The composition of claim 2 wherein said support component comprises $Al_2O_3$ or anatase $TiO_2$.

4. The composition of claim 1 wherein said support component comprises oxygen-functionalized multi-walled carbon nanotubes or oxygen-functionalized activated carbon.

5. The composition of claim 1 wherein the composition is the reaction product of $MoO_2Cl_2$ (dme) and the support component is selected from oxygen-functionalized activated carbon, $Al_2O_3$, anatase $TiO_2$ and oxygen-functionalized multi walled carbon nanotubes.

6. The composition of claim 4 wherein the molybdenum dioxo moiety is coupled to the oxygen-functionalized activated carbon, said composition absent chloride.

7. The composition of claim 6 wherein said Mo dioxo moiety comprises up to about 5.0 wt. % of said composition.

8. A method of producing hydrogen and an aldehyde from methanol or ethanol, said method comprising:
   providing a reaction medium comprising an alcohol selected from methanol, ethanol and a combination thereof; and
   contacting said medium with the composition of claim 1, said contact for a time and at a temperature sufficient to oxidize said alcohol to said aldehyde and produce hydrogen gas.

9. The method of claim 8 wherein said alcohol is provided as a neat alcohol, an alcohol in an organic solvent, or an aqueous solution of an alcohol.

10. The method of claim 9 wherein said alcohol is provided as an aqueous solution of the alcohol, comprising up to about 90% water.

11. The method of claim 8 wherein said alcohol is provided in toluene.

12. The method of claim 8 wherein said reaction medium is at a temperature less than about 100° C.

13. The method of claim 8 comprising regeneration of said composition, said regeneration by at least one of providing a said alcohol as an aqueous solution and washing said composition after reaction with said alcohol.

14. The method of claim 8 incorporated into a process selected from batch, semi-batch and continuous processes.

15. The method of claim 8 substantially absent production of carbon monoxide or carbon dioxide.

16. A method of producing hydrogen and an aldehyde from methanol or ethanol, said method comprising:
   providing a reaction medium comprising an alcohol selected from methanol, ethanol and a combination thereof; and
   contacting said medium with the composition of claim 5, said contact for a time and at a temperature sufficient to oxidize said alcohol to said aldehyde and produce hydrogen gas.

17. A method of producing hydrogen and an aldehyde from methanol or ethanol without production of carbon monoxide or carbon dioxide, said method comprising:
   providing a reaction medium comprising a composition comprising water and an alcohol selected from methanol and ethanol and a combination thereof, said composition comprising up to about 90% water; and
   contacting said medium with the composition of claim 6, said contact for a time and at a temperature sufficient to oxidize a said alcohol to a said aldehyde and produce hydrogen gas substantially without production of carbon monoxide or carbon dioxide.

18. The method of claim 17 wherein said reaction medium is at a temperature less than about 100° C.

19. The method of claim 17 comprising regeneration of said composition, said regeneration by at least one of providing a said alcohol as an aqueous solution and washing said composition after reaction with said alcohol.

20. The method of claim 17 incorporated into a process selected from batch, semi-batch and continuous processes.

21. A composition comprising a molybdenum dioxo moiety coupled to a support component comprising an oxygen moiety, said composition absent an $MoO_3$ moiety, wherein said support component comprises oxygen-functionalized activated carbon, wherein said composition is absent chloride, and wherein the density of said Mo dioxo moiety on said oxygen-functionalized activated carbon is up to about 0.22 $Mo/nm^2$.

22. The composition of claim 21 wherein said Mo dioxo moiety comprises up to about 2.5 wt. % of said composition.

23. The composition of claim 22 wherein said Mo dioxo moiety comprises about 2.1 wt. % of said composition.

24. The composition of claim 23 wherein the density of said Mo dioxo moiety on said activated carbon is about 0.10 $Mo/nm^2$.

* * * * *